United States Patent
Motomura et al.

(10) Patent No.: US 9,330,455 B2
(45) Date of Patent: May 3, 2016

(54) DIAGNOSTIC SUPPORT APPARATUS AND DIAGNOSTIC SUPPORT METHOD

(71) Applicant: PANASONIC CORPORATION, Osaka (JP)

(72) Inventors: Hideto Motomura, Kyoto (JP); Yoshikuni Sato, Fukui (JP); Kazuki Kozuka, Fukui (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 123 days.

(21) Appl. No.: 14/066,770

(22) Filed: Oct. 30, 2013

(65) Prior Publication Data

US 2014/0072193 A1   Mar. 13, 2014

Related U.S. Application Data

(63) Continuation of application No. PCT/JP2012/007163, filed on Nov. 8, 2012.

(30) Foreign Application Priority Data

Nov. 24, 2011   (JP) .................................. 2011-256834

(51) Int. Cl.
*G06T 7/00* (2006.01)
*A61B 6/00* (2006.01)
(Continued)

(52) U.S. Cl.
CPC ............... *G06T 7/0012* (2013.01); *A61B 5/055* (2013.01); *A61B 6/032* (2013.01); *A61B 6/037* (2013.01);
(Continued)

(58) Field of Classification Search
None
See application file for complete search history.

(56) References Cited

U.S. PATENT DOCUMENTS 5,343,390 A * 8/1994 Doi ....................... G06F 19/345
378/901
5,359,513 A  10/1994 Kano et al.
(Continued)

FOREIGN PATENT DOCUMENTS

JP   07-037074    2/1995
JP   07-335721   12/1995
(Continued)

OTHER PUBLICATIONS

W Zhang, K Doi, ML Giger, Y Wu, RM Nishikawa, and RA Schmidt, "Computerized detection of clustered microcalcifications in digital mammograms using a shift-invariant artificial neural network," Medical Physics 21, 517 (1994); doi: 10.1118/1.597177.*

(Continued)

*Primary Examiner* — Matthew Bella
*Assistant Examiner* — Soo Shin
(74) *Attorney, Agent, or Firm* — Wenderoth, Lind & Ponack, L.L.P.

(57) ABSTRACT

The diagnostic support apparatus includes a feature quantity calculation unit vectorizing a test image into shift-invariant feature quantities, a base representation unit transforming the shift-invariant feature quantities of the test image into a linear combination of base vectors with first coefficients, the base vectors being calculated from a plurality of vectors representing shift-invariant feature quantities of a plurality of normal structural images including no lesion site, a lesion determination unit determining that the test image includes a lesion site when a difference between the first coefficients and second coefficients is greater than a determination threshold value, the second coefficients being used to transform shift-invariant feature quantities calculated from one of the normal structural images into a linear combination of the base vectors, and an output unit outputting a result of the determination by the lesion determination unit.

10 Claims, 16 Drawing Sheets

(51) Int. Cl.
   *A61B 5/055* (2006.01)
   *A61B 6/03* (2006.01)
   *A61B 8/08* (2006.01)

(52) U.S. Cl.
   CPC .. *A61B 6/50* (2013.01); *A61B 8/085* (2013.01); *A61B 2576/00* (2013.01); *G06T 2207/10072* (2013.01); *G06T 2207/20064* (2013.01); *G06T 2207/30064* (2013.01)

(56) References Cited

U.S. PATENT DOCUMENTS

| | | | |
|---|---|---|---|
| 5,475,268 A | 12/1995 | Kawagoe et al. | |
| 5,491,627 A * | 2/1996 | Zhang | G06F 19/345 128/924 |
| 5,627,907 A * | 5/1997 | Gur | G06K 9/00127 382/132 |
| 6,192,150 B1 * | 2/2001 | Leow | G06F 17/30262 382/181 |
| 6,915,003 B2 | 7/2005 | Oosawa | |
| 7,616,789 B2 | 11/2009 | Oosawa | |
| 8,005,319 B2 * | 8/2011 | Lin | G06T 3/0031 382/299 |
| 8,238,673 B2 | 8/2012 | Mitarai et al. | |
| 2001/0048757 A1 | 12/2001 | Oosawa | |
| 2003/0210813 A1 | 11/2003 | Oosawa | |
| 2007/0189594 A1 | 8/2007 | Oosawa | |
| 2008/0253665 A1 | 10/2008 | Mitarai et al. | |
| 2009/0297048 A1 * | 12/2009 | Slotine | G06K 9/4671 382/224 |
| 2010/0104148 A1 * | 4/2010 | Bovik | G06K 9/4633 382/128 |
| 2010/0142786 A1 | 6/2010 | Degani et al. | |
| 2010/0189320 A1 * | 7/2010 | Dewaele | G06T 7/0081 382/128 |
| 2010/0266179 A1 * | 10/2010 | Ramsay | G06T 7/0012 382/131 |
| 2010/0278425 A1 * | 11/2010 | Takemoto | G06T 7/0079 382/173 |
| 2012/0088981 A1 * | 4/2012 | Liu | G06K 9/6215 600/300 |
| 2012/0166142 A1 * | 6/2012 | Maeda | G05B 23/0227 702/185 |
| 2012/0183225 A1 * | 7/2012 | Pal | G06K 9/4614 382/195 |
| 2012/0283574 A1 * | 11/2012 | Park | G06K 9/46 600/476 |
| 2013/0197384 A1 * | 8/2013 | Tang | G01N 33/497 600/532 |

FOREIGN PATENT DOCUMENTS

| | | |
|---|---|---|
| JP | 2002-032735 | 1/2002 |
| JP | 2004-041694 | 2/2004 |
| JP | 2006-325937 | 12/2006 |
| JP | 2008-282391 | 11/2008 |
| JP | 2011-014152 | 1/2011 |

OTHER PUBLICATIONS

D Tahmoush, "Image similarity to improve the classification of breast cancer images," Algorithms 2009, 2, 1503-1525; doi:10.3390/a2041503.*
Stork, et al. WO 01/39123, May 31, 2001.*
International Search Report issued Jan. 15, 2013 in International (PCT) Application No. PCT/JP2012/007163.
Bram van Ginneken et al., "Automatic Detection of Abnormalities in Chest Radiographs Using Local Texture Analysis", IEEE Transactions on Medical Imaging, vol. 21, No. 2, Feb. 2002, pp. 139-149.
Hisanaga Fujiwara et al., "Textile Surface Inspection by Using Translation Invariant Wavelet Shrinkage", The transactions of the Institute of Electrical Engineers of Japan. D, A publication of Industry Applications Society 126(1), pp. 25-34, Jan. 1, 2006.

* cited by examiner

Spatial frequency vector F

DIAGNOSTIC SUPPORT APPARATUS AND DIAGNOSTIC SUPPORT METHOD

CROSS REFERENCE TO RELATED APPLICATIONS

This is a continuation application of PCT International Application No. PCT/JP2012/007163 filed on Nov. 8, 2012, designating the United States of America, which is based on and claims priority of Japanese Patent Application No. 2011-256834 filed on Nov. 24, 2011. The entire disclosures of the above-identified applications, including the specifications, drawings and claims are incorporated herein by reference in their entirety.

FIELD

One or more exemplary embodiments disclosed herein relate generally to a diagnostic support apparatus and method that support image-based diagnosis by doctors.

BACKGROUND

In order to support image-based diagnosis by doctors, apparatuses for comparing a test image that is a medical image of a subject to be tested with normal structural images that are medical images of normal structures so as to determine the presence or absence of a lesion site have conventionally been proposed (see Patent Literatures 1 to 3, for example).

CITATION LIST

Patent Literature

[PTL 1]
  Japanese Unexamined Patent Application Publication No. 7-37074
[PTL 2]
  Japanese Unexamined Patent Application Publication No. 2002-32735
[PTL 3]
  Japanese Unexamined Patent Application Publication No. 2004-41694

SUMMARY

The conventional apparatuses, however, require alignment between the test image and the normal structural images and accordingly may have reduced precision in determining the presence or absence of a lesion site if the alignment is not accurate.

One non-limiting and exemplary embodiment provides a diagnostic support apparatus that has high precision in determining the presence or absence of a lesion site.

In one general aspect, the techniques disclosed here feature a diagnostic support apparatus that include a feature quantity calculation unit configured to vectorize a test image into shift-invariant feature quantities, the test image being an image in which presence of a lesion site is unknown, a base representation unit configured to transform the shift-invariant feature quantities of the test image into a linear combination of base vectors with first coefficients, the base vectors being calculated from a plurality of vectors representing shift-invariant feature quantities of a plurality of normal structural images that include no lesion site, a lesion determination unit configured to determine that the test image includes a lesion site when a difference between the first coefficients and second coefficients is greater than a determination threshold value, the second coefficients being used to transform shift-invariant feature quantities calculated from one of the plurality of normal structural images into a linear combination of the base vectors, and an output unit configured to output a result of the determination by the lesion determination unit.

With this configuration, the comparison between the test image and the normal structural images is made by comparing the first and second coefficients used to transform the shift-invariant feature quantities to a base representation. The presence or absence of a lesion can thus be determined without requiring alignment between the test image and the normal structural images. Eliminating an alignment process prevents a reduction in precision in determining the presence or absence of a lesion site due to the use of different methods for setting landmarks or due to variations in setting positions of landmarks, thus making it possible to provide a diagnostic support apparatus having high precision in determining the presence or absence of a lesion site.

These general and specific aspects may be implemented using a system, a method, an integrated circuit, a computer program, or a computer-readable recording medium such as a CD-ROM, or any combination of systems, methods, integrated circuits, computer programs, or computer-readable recording media.

Additional benefits and advantages of the disclosed embodiments will be apparent from the Specification and Drawings. The benefits and/or advantages may be individually obtained by the various embodiments and features of the Specification and Drawings, which need not all be provided in order to obtain one or more of such benefits and/or advantages.

One or more exemplary embodiments or features disclosed herein provide a diagnostic support apparatus having high precision in determining the presence or absence of a lesion site.

BRIEF DESCRIPTION OF DRAWINGS

These and other advantages and features will become apparent from the following description thereof taken in conjunction with the accompanying Drawings, by way of non-limiting examples of embodiments disclosed herein.

Figure 1:
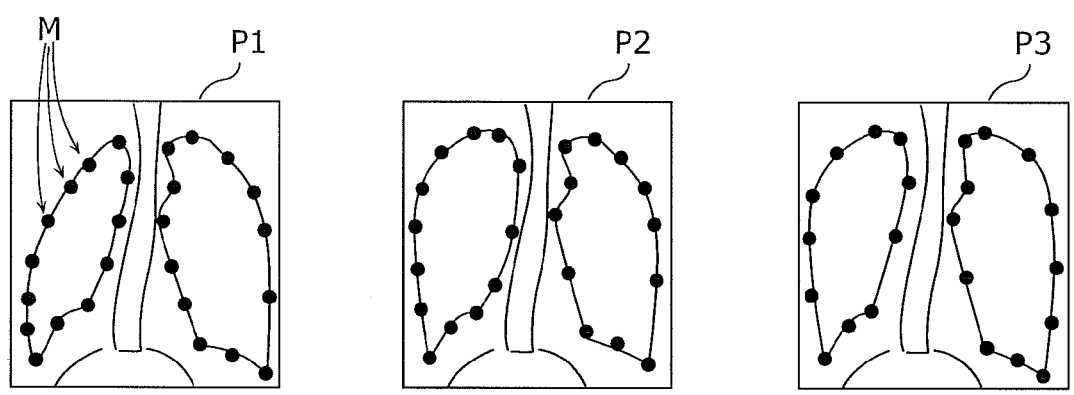
FIG. 1 is a diagram for explaining the setting of landmarks in Patent Document 1.

DETAILED DESCRIPTION OF THE INVENTION (Underlying Knowledge Forming Basis of the Present Disclosure)

In relation to the conventional apparatus disclosed in the Background section, the inventors have found the following problem:

Medical practices are roughly divided into two parts, diagnosis practices and treatment practices.

The purpose of the diagnostic practices is diagnosing a disease and grasping the condition of the disease, and a treatment plan is determined in accordance with the name and condition of the disease. Initial implementation of the diagnostic practices involves examination by interview and palpation, and in the case of suspected diseases, more detailed tests are carried out in image-based diagnosis. In the image-based diagnosis, the condition of the body is examined by a nondestructive test using radiation or ultrasound, for example. The surfaces of the internal organs are also observed with an endoscope or the like. In order to diagnose a disease and grasp the condition of the disease, pathological diagnosis is carried out, in which a specimen is extracted from a lesion site and the condition of the specimen is observed at a cellular level. The extracted specimen is sliced to a thickness that can be observed with a microscope, making a preparation. The made preparation is shot by a digital camera or read by a scanner under the microscope, and the obtained image is stored as a digital image for later reference.

Such digitization of medical images improves consistency between the medical images and data processing by computers and is increasing opportunities for IT systems to support diagnostic practices by doctors and technicians. One example is computer-aided design (CAD), which is a method of utilizing computers for detection of a lesion site.

Diagnosticians usually remember medical images of normal structures that include no lesion sites. When a test image that is a medical image of a subject to be tested is presented, diagnosticians think of normal structural images, which are medical images of normal structures, and compares the test image with the normal structural images. When having found a difference between the test image and the normal structural images, the diagnosticians determine that the area of difference is a lesion site. Calculating a difference between two pieces of data is a basic function in computer processing, and therefore, the image-based diagnosis in which a lesion area is detected by the comparison between a test image and normal structural images is what the computer processing is good at.

Such difference calculations, however, require alignment between a test image and normal structural images. To create the normal structural images, usually past medical images are used. Specifically, a diagnostician checks a test image and finds no lesion site therein, the test image is regarded as a normal structural image. If past test images of a patient include no lesion site, these test images can be used as normal structural images. However, the positions of a test image and normal structural images of even the same patient usually do not match due to various factors such as different shooting conditions or changes in the patient's shape. In addition, normal structural images cannot be obtained when a test image is captured for the first time, because there are no images to be compared. In this case, normal structural images of other patients are used, but alignment between the test image and these normal structural images becomes necessary due to a difference in shape from the other patients.

The alignment is specifically implemented by geometric transformation such as rotation, parallel displacement, and enlargement and reduction. For example, a plurality of corresponding points are set for each of a test image and a normal structural image, and one of the images is subjected to affine transformation and enlargement/reduction processing so that the corresponding points of the images match. Alternatively, the alignment may also be performed using a nonlinear transformation method in which template matching is performed for each local area, or using a transformation method in which perspective matching and local alignment are used in combination, as disclosed in Patent Documents 1 and 2, for example.

Incidentally, normal structural images are generated from images that were captured in the past and have already been checked that no lesions are included. One reason for this is, as described above, that a test image of a patient captured for the first time has no medical images to be compared. The other reason is that medical knowledge tends to be built up by accumulation of knowledge from past cases and it is more likely that generating normal structural images having no lesions from past cases will have higher medical utility values. The medical knowledge is making steady improvement, and the interpretation of past cases is often improved. Therefore, the medical knowledge registered in IT systems always needs updating, and even normal structural images are no exceptions.

In view of this, it is desirable to collect normal structural images of a plurality of patients and generate highly versatile normal structural images that can comprehensively express these collected images. One specific example of the method for implementing such generation is expressing a normal structural image as a linear combination of an average shape and an eigen shape, as disclosed in Patent Document 3. In other words, a shape vector x representing a normal structure is expressed using Expression 1 below.

$$x = x_{ave} Ps \cdot bs \qquad [\text{Expression 1}]$$

Here, $x_{ave}$ is the average shape vector, Ps is the eigen shape vector, and bs is a set of shape coefficients.

The average shape vector $x_{ave}$ and the eigen shape vector Ps are necessary for the calculation using Expression 1, and landmarks M as shown in FIG. 1 are set in an image to vectorize image information. The landmarks M are indicated by black dots in FIG. 1. The image information is vectorized using the xy coordinates of the landmarks M as vector elements. As shown in test images P1, P2, and P3, the setting of landmarks and the definition of shape vectors are individually performed for a plurality of normal structural images, and these landmarks and shape vectors are used to calculate the average vector and the eigen vector. Note that test images can also similarly be expressed using Expression 1.

Using the vectors described above, a test image and normal structural images are aligned and a lesion site is detected from a difference between the test image and the normal structural images. This supports image-based diagnosis.

However, with the conventional technology, the task of setting landmarks is complicated and leads to a reduction in the efficiency of the diagnostic practices. Changing the method for setting landmarks alters the xy coordinates of landmarks and accordingly alters vector elements. Consequently, the average shape vector and the eigen shape vector differ from those before the change of the method for setting landmarks. Patent Document 3 does not disclose any method for setting landmarks, and therefore, even if the same technique is used, various normal structural images (shape vectors representing normal structures) will be generated due to the use of different methods for setting landmarks or due to variations in set positions of landmarks. Since the medical knowledge is built up by the accumulation of knowledge from past cases, the fact that a given case is defined in various ways depending on the method for setting landmarks is undesirable in terms of reusability. If a single case is defined in various ways as described above, the precision in determining the presence or absence of a lesion site will be reduced. In other words, the same test image may be determined as a lesion image or a normal image depending on the definition.

According to an exemplary embodiment disclosed herein, diagnostic support apparatus includes a feature quantity calculation unit configured to vectorize a test image into shift-invariant feature quantities, the test image being an image in which presence of a lesion site is unknown, a base representation unit configured to transform the shift-invariant feature quantities of the test image into a linear combination of base vectors with first coefficients, the base vectors being calculated from a plurality of vectors representing shift-invariant feature quantities of a plurality of normal structural images that include no lesion site, a lesion determination unit configured to determine that the test image includes a lesion site when a difference between the first coefficients and second coefficients is greater than a determination threshold value, the second coefficients being used to transform shift-invariant feature quantities calculated from one of the normal structural images into a linear combination of the base vectors, and an output unit configured to output a result of the determination by the lesion determination unit.

With this configuration, the comparison between the test image and the normal structural images is made by comparing the first and second coefficients used to transform the shift-invariant feature quantities to a base representation. The presence or absence of a lesion can thus be determined without requiring alignment between the test image and the normal structural images. Eliminating an alignment process prevents a reduction in precision in determining the presence or absence of a lesion site due to the use of different methods for setting landmarks or due to variations in setting positions of landmarks, thus making it possible to provide a diagnostic support apparatus having high precision in determining the presence or absence of a lesion site.

For example, the feature quantity calculation unit may be configured to calculate a plurality of shift-invariant feature quantities from a pixel of interest in the test image and calculate a test image feature quantity vector having the calculated shift-invariant feature quantities as vector elements, the base representation unit may be configured to calculate the first coefficients and calculate a test coefficient vector having the calculated first coefficients as vector elements, the first coefficients being used to represent the test image feature quantity vector as the linear combination of the base vectors, the base vectors being calculated from a plurality of image feature quantity vectors each having, as vector elements, shift-invariant feature quantities calculated from pixels in each of the normal structural images, the normal structural images each being a medical image of a normal structure, the diagnostic support apparatus may further include a nearest neighbor vector detection unit configured to detect a normal coefficient vector that is most similar to the test coefficient vector as a nearest neighbor vector from among a plurality of normal coefficient vectors each having second coefficients as vector elements, the second coefficients being used to represent each of the image feature quantity vectors as a linear combination of the base vectors, and the lesion determination unit may be configured to compare a distance between the test coefficient vector and the nearest neighbor vector with the determination threshold value, determine that the pixel of interest is in the lesion site when the distance is greater than the determination threshold value, and determine that the pixel of interest is in a normal site when the distance is smaller than or equal to the determination threshold value.

With this configuration, the comparison between the test image and the normal structural images is made by comparing the coefficient vectors, using the shift-invariant feature quantities. This eliminates the need for alignment between the normal structural image and the test image and makes it possible to determine the presence or absence of a lesion. The elimination of the need for the alignment process avoids the possibility of a reduction in the precision in determining a lesion site due to the use of different methods of setting landmarks or due to variations in the positions to set landmarks, thus making it possible to provide a diagnostic support apparatus having high precision in determining a lesion site.

The shift-invariant feature quantities may be ones of wavelet coefficients, higher order local auto correlation (HLAC) feature quantities, scale invariant feature transform (SIFT) feature quantities, and histogram of oriented gradients (HOG) feature quantities.

With this configuration, the image information can be vectorized without depending on the positions of pixels. This eliminates the need for an alignment process using landmarks, for example.

The medical image may be one of a radiological image, an ultrasound image, and a pathological specimen image.

With this configuration, it is possible to use any medical image that is necessary to diagnose a disease and grasp the condition of the disease and to thereby improve the efficiency and quality of the support of diagnosis.

The nearest neighbor vector detection unit may be configured to detect, as the nearest neighbor vector, a normal coefficient vector that is most similar to the test coefficient vector from among a plurality of normal coefficient vectors corresponding to a plurality of pixels in the normal structural images, the pixels being located within a predetermined range of distances from the pixel of interest.

With this configuration, it is possible to limit normal coefficient vectors to be referenced and to thereby shorten the time required to detect the nearest neighbor vector.

The determination threshold value may be either an average or median value of distances between a lesion coefficient vector and a nearest neighbor vector that is most similar to the lesion coefficient vector among the normal coefficient vectors, the lesion coefficient vector having, as vector elements, coefficients with which a lesion image feature quantity vector is represented as a linear combination of the base vectors, the lesion image feature quantity vector having, as vector elements, shift-invariant feature quantities calculated from a pixel in a lesion site.

With this configuration, it is possible to make medically highly accurate determinations that are proven by past diagnostic results.

The lesion determination unit may be further configured to determine occurrence of a detection error when a distance between the pixel of interest and a pixel used to calculate the nearest neighbor vector is greater than a detection error threshold value.

If the distance is too great, it is more likely that the nearest neighbor vector is detected from a pixel in a different internal organ from the internal organ in which the pixel of interest is included, and accordingly, it is difficult to accurately determine the presence or absence of a lesion. In view of this, the detection error threshold value is provided in order to make it possible to improve the precision in determining the presence or absence of a lesion.

The feature quantity calculation unit may be configured to calculate a plurality of shift-invariant feature quantities from a pixel of interest in the test image and calculate a test image feature quantity vector having the calculated shift-invariant feature quantities as vector elements, the base representation unit may be configured to calculate the first coefficients and calculate a test coefficient vector having the calculated first coefficients as vector elements, the first coefficients being used to represent the test image feature quantity vector as a linear combination of the base vectors, the base vectors being calculated from a plurality of image feature quantity vectors each having, as vector elements, shift-invariant feature quantities calculated from pixels in each of the normal structural images, and the normal structural images each being a medical image of a normal structure, the diagnostic support apparatus may further include a neighbor vector detection unit configured to detect a predetermined number of normal coefficient vectors starting from a normal coefficient vector that is most similar to the test coefficient vector from among a plurality of normal coefficient vectors each having second coefficients as vector elements, the second coefficients being used to represent each of the image feature quantity vectors as the linear combination of the base vectors, and the lesion determination unit may be configured to, for each of the predetermined number of normal coefficient vectors detected by the neighbor vector detection unit, compare a distance between the test coefficient vector and the normal coefficient vector with the determination threshold value, determine that the pixel of interest is in the lesion site when the distance is greater than the determination threshold value, and determine that the pixel of interest is in a normal site when the distance is smaller than or equal to the determination threshold value. With this configuration, it is possible not only to output the determination result obtained from the normal structural image that is most similar to the test image but also to output determination results obtained from normal structural images that are second and subsequent most similar to the test image.

These general and specific aspects may be implemented using a system, a method, an integrated circuit, a computer program, or a computer-readable recording medium such as a CD-ROM, or any combination of systems, methods, integrated circuits, computer programs, or computer-readable recording media.

Hereinafter, certain exemplary embodiments are described in greater detail with reference to the accompanying drawings.

Each of the exemplary embodiments described below shows a general or specific example. The numerical values, shapes, materials, structural elements, the arrangement and connection of the structural elements, steps, the processing order of the steps etc. shown in the following exemplary embodiments are mere examples, and therefore do not limit the scope of the appended Claims and their equivalents. Therefore, among the structural elements in the following exemplary embodiments, structural elements not recited in any one of the independent claims are described as arbitrary structural elements.

Embodiment 1

The present embodiment describes a diagnostic support apparatus that eliminates the need to set corresponding points for alignment by transforming image information to a vector expression using, as vector elements, shift-invariant feature quantities that do not depend on the position of a target subject.

Figure 2:
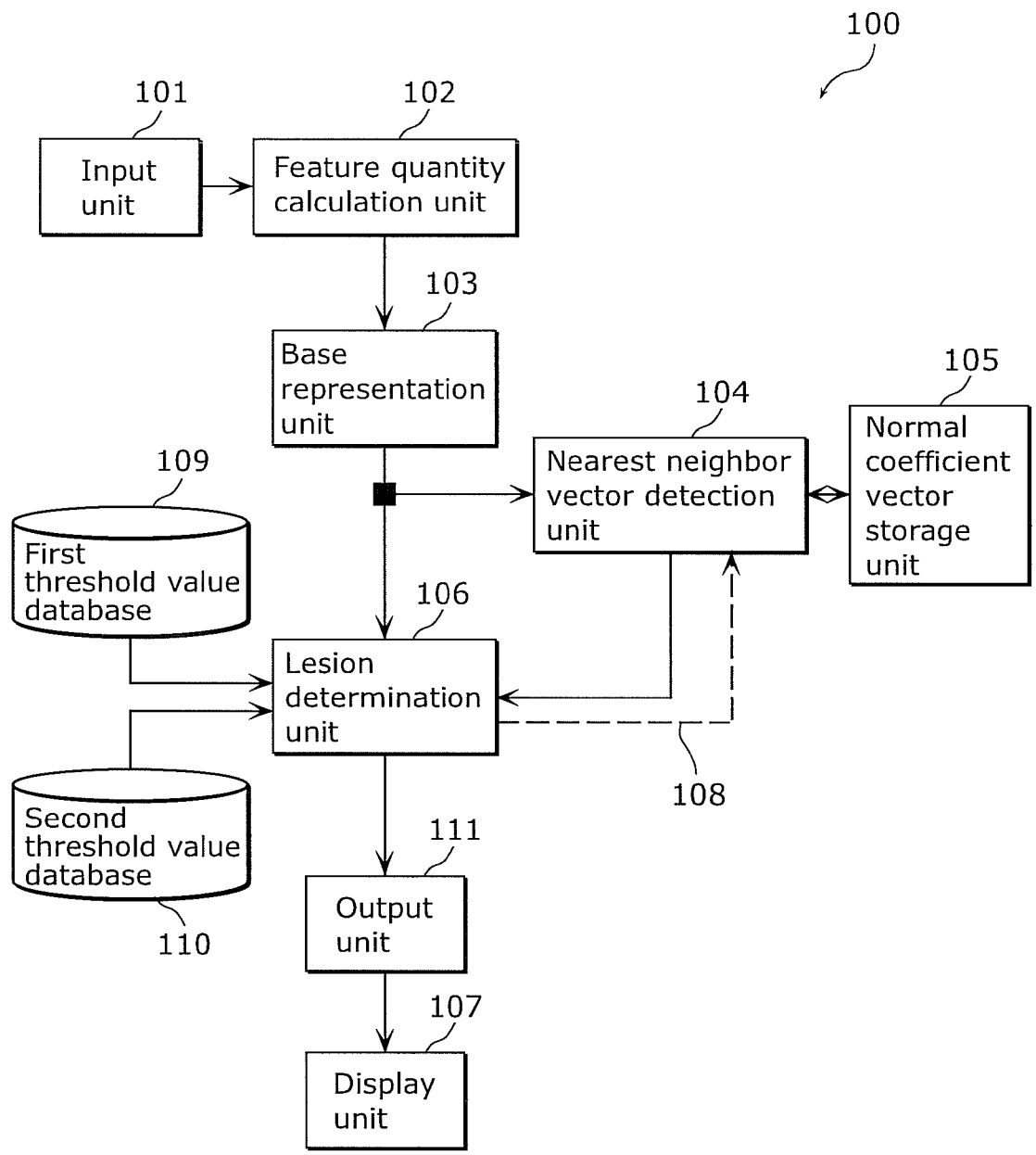
FIG. 2 is a block diagram showing a functional configuration of a diagnostic support apparatus according to Embodiment 1.

FIG. 2 is a block diagram showing a functional configuration of the diagnostic support apparatus according to Embodiment 1.

A diagnostic support apparatus 100 includes an input unit 101, a feature quantity calculation unit 102, a base representation unit 103, a nearest neighbor vector detection unit 104, a normal coefficient vector storage unit 105, a lesion determination unit 106, an output unit 111, and a display unit 107, and is configured to detect a lesion site that is an area of difference between a test image and normal structural images.

The input unit 101 is configured to receive a test image that is a medical image necessary for diagnosis. In the present embodiment, no restrictions are put on the type of medical images, and any medical image can be used as a target. Examples of the target include computer tomography (CT) images, magnetic resonance (MR) images, positron emission tomography (PET) images, ultrasound images, pathological images, and plain radiographic images of the chest that are kinds of radiological images.

The feature quantity calculation unit 102 is configured to calculate a plurality of shift-invariant feature quantities from a pixel of interest in the test image and calculate a test image feature quantity vector having the calculated shift-invariant feature quantities as its vector elements. In other words, the feature quantity calculation unit 102 is configured to vectorize image information on the test image, using the shift-invariant feature quantities and output test image feature quantity vectors $f_p$. The feature quantity calculation unit 102 is configured to output a test image feature quantity vector $f_p$ for each pixel in the test image.

Figure 3:
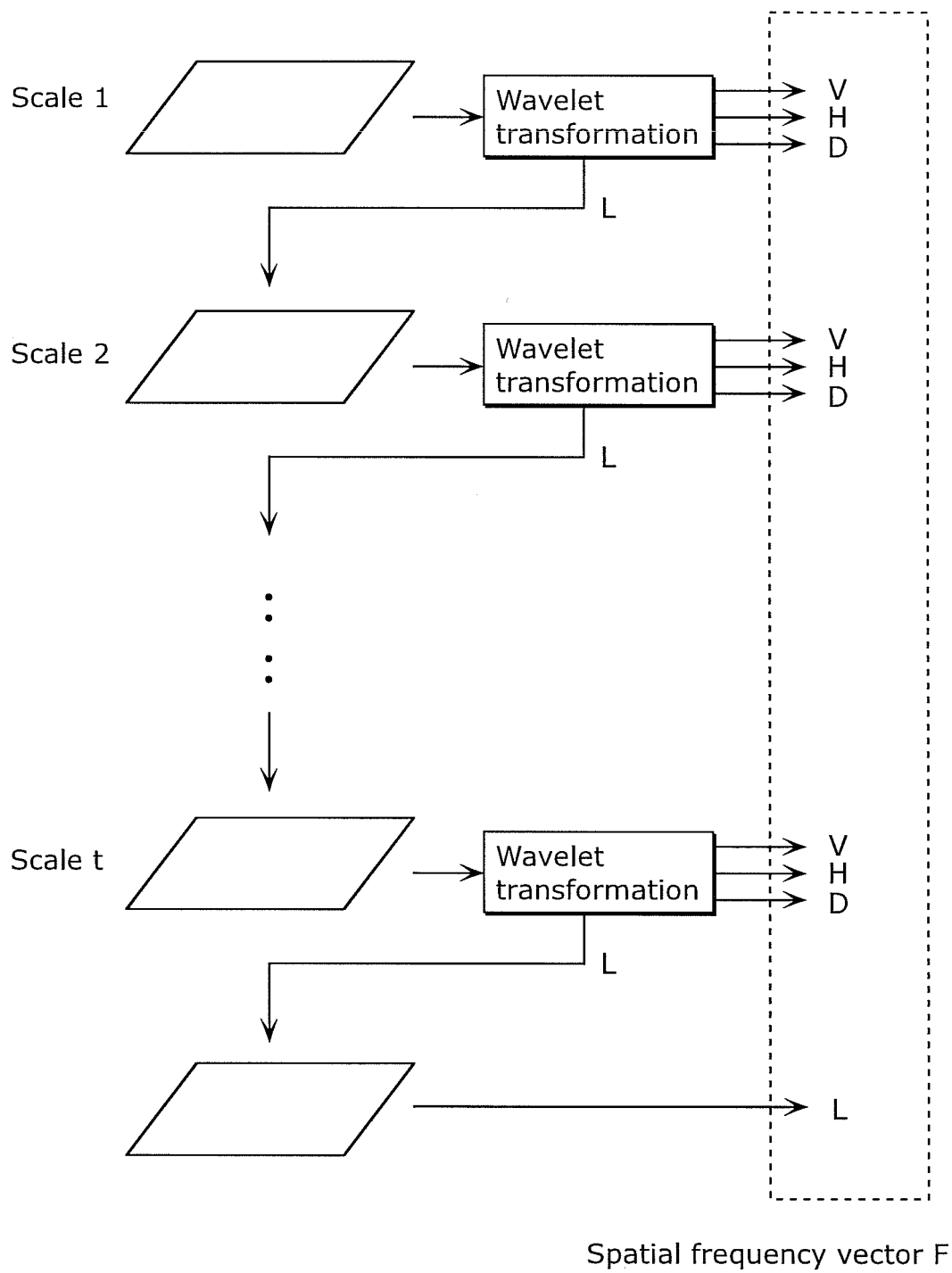
FIG. 3 shows an example of calculation of a shift-invariant feature quantity through wavelet transformation.

Here, the method for calculating shift-invariant feature quantities from a group of pixel values will be described, taking wavelet transformation as an example. FIG. 3 shows an example of the calculation of shift-invariant feature quantities through the wavelet transformation. The feature quantity calculation unit 102 provides multiresolution representation of the test image in t scales through the wavelet transformation. In scale 1, differences in luminance between adjacent pixels are calculated, and smoothing is performed on a plurality of pixels at the time of transition to scale 2. In scale 2, differences in luminance between adjacent pixels are also calculated, but it is noted that each pixel of scale 2 is obtained by smoothing a plurality of pixels of scale 1 and accordingly has a lower frequency component. Therefore, carrying out the calculations from scale 1 to scale t (t is an integer of 2 or more) yield wavelet coefficients V, H, and D of each scale with gradual transition from high frequency components to low frequency components. The feature quantity calculation unit 102 generates, for each pixel, a spatial frequency vector F consisting of the wavelet coefficients V, H, and D calculated in each scale and an average luminance value L calculated from the image of scale t. In other words, the number of dimensions of the spatial frequency vector F is (3t+1).

Figure 4A:
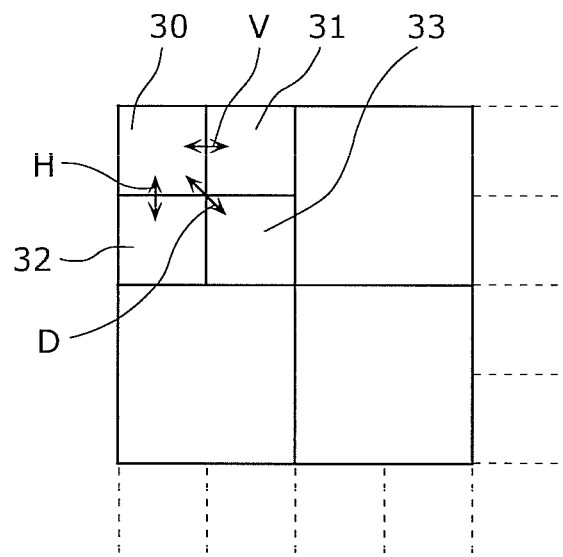
FIGS. 4A and 4B show an example of calculation of wavelet coefficients using Haar mother wavelet transform.
Figure 4B:
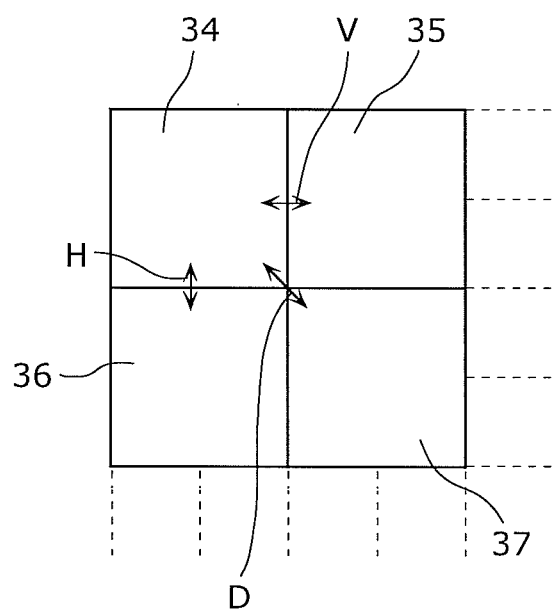

In the case of using Haar mother wavelet transform, as shown in FIG. 4A, V is the luminance difference value between a pixel of interest 30, which is a pixel to be processed, and a right adjacent pixel 31, H is the luminance difference value between the pixel of interest 30 and a bottom adjacent pixel 32, D is the luminance difference value between the pixel of interest 30 and a lower-right diagonally adjacent pixel 33, and L is the average luminance value of the four pixels including the pixel of interest 30, the right adjacent pixel 31, the bottom adjacent pixel 32, and the lower-right diagonally adjacent pixel 33. FIG. 4A corresponds to scale 1, and FIG. 4B corresponds to scale 2. The test image of scale 2 is an image in which each pixel has an average luminance value of four pixels in the test image of scale 1. In other words, in scale 2, the luminance value of each block for which the luminance difference value is the output L, which is the average luminance value of four pixels in the image of scale 1. The output V in scale 2 is a luminance difference value between a block 34 and a right adjacent block 35. The output H in scale 2 is a luminance difference value between the block 34 and a bottom adjacent block 36. The output D in scale 2 is a luminance difference value between the block 34 and a lower-right adjacent block 37. The output L in scale 2 is an average luminance value of the four blocks including the block 34, the right adjacent block 35, the bottom adjacent block 36, and the lower-right adjacent block 37.

As described above, in the case of using the wavelet transformation, the test image feature quantity vectors $f_p$ are calculated as the spatial frequency vectors F in FIG. 3.

While the wavelet coefficients are used as the shift-invariant feature quantities in the present embodiment, the shift-invariant feature quantities are not limited thereto, and any shift-invariant feature quantities can be used. Examples of the shift-invariant feature quantities include SIFT feature quantities, HLAC feature quantities, and HOG feature quantities.

The base representation unit 103 is configured to transform the test image feature quantity vectors $f_p$ to a base vector representation and output test coefficient vectors $\alpha_p$. In other words, the base representation unit 103 is configured to calculate coefficients (first coefficients) used to represent a test image feature quantity vector $f_p$ as a linear combination of base vectors, and calculate a test coefficient vector $\alpha_p$ having the calculated coefficients as its vector elements, the base vectors being calculated from a plurality of image feature quantity vectors each having, as its vector elements, shift-invariant feature quantities calculated from pixels in each of a plurality of normal structural images. The base representation unit 103 transforms the test image feature quantity vectors $f_p$ into the test coefficient vectors $\alpha_p$, using Expression 2 below.

$$\alpha_p = B^{-1}(f_p - g) \qquad \text{[Expression 2]}$$

$$\Leftrightarrow \begin{pmatrix} \alpha_{p,1} \\ \alpha_{p,2} \\ \vdots \\ \alpha_{p,n} \end{pmatrix} = (b_1 \ b_2 \ \ldots \ b_n)^{-1}(f_p - g)$$

$$\Leftrightarrow \begin{pmatrix} \alpha_{p,1} \\ \alpha_{p,2} \\ \vdots \\ \alpha_{p,n} \end{pmatrix} = \begin{pmatrix} b_{1,1} & b_{2,1} & \ldots & b_{n,1} \\ b_{1,2} & b_{2,2} & \ldots & b_{n,2} \\ \vdots & \vdots & \vdots & \vdots \\ b_{1,n} & b_{2,n} & \ldots & b_{n,n} \end{pmatrix}^{-1} \begin{pmatrix} f_{p,1} - g_1 \\ f_{p,2} - g_2 \\ \vdots \\ f_{p,n} - g_n \end{pmatrix}$$

Here, a matrix B represents a normal structural base vector matrix, which will be described later, and a vector g represents an average normal structural vector, which will be described later. Expression 2 is obtained by solving Expression 1 for a shape coefficient set bs. The correspondence between Expression 1 and Expression 2 is as follows:

Shape Vector x ⇔ Test Image Feature Quantity Vector $f_p$

Average Shape Vector $x_{ave}$ ⇔ Average Normal Structural Vector g

Eigen shape vector Ps ⇔ Normal Structural Base Vector Matrix B

Shape Coefficient Set bs ⇔ Test Coefficient Vector $\alpha_p$

Figure 5:
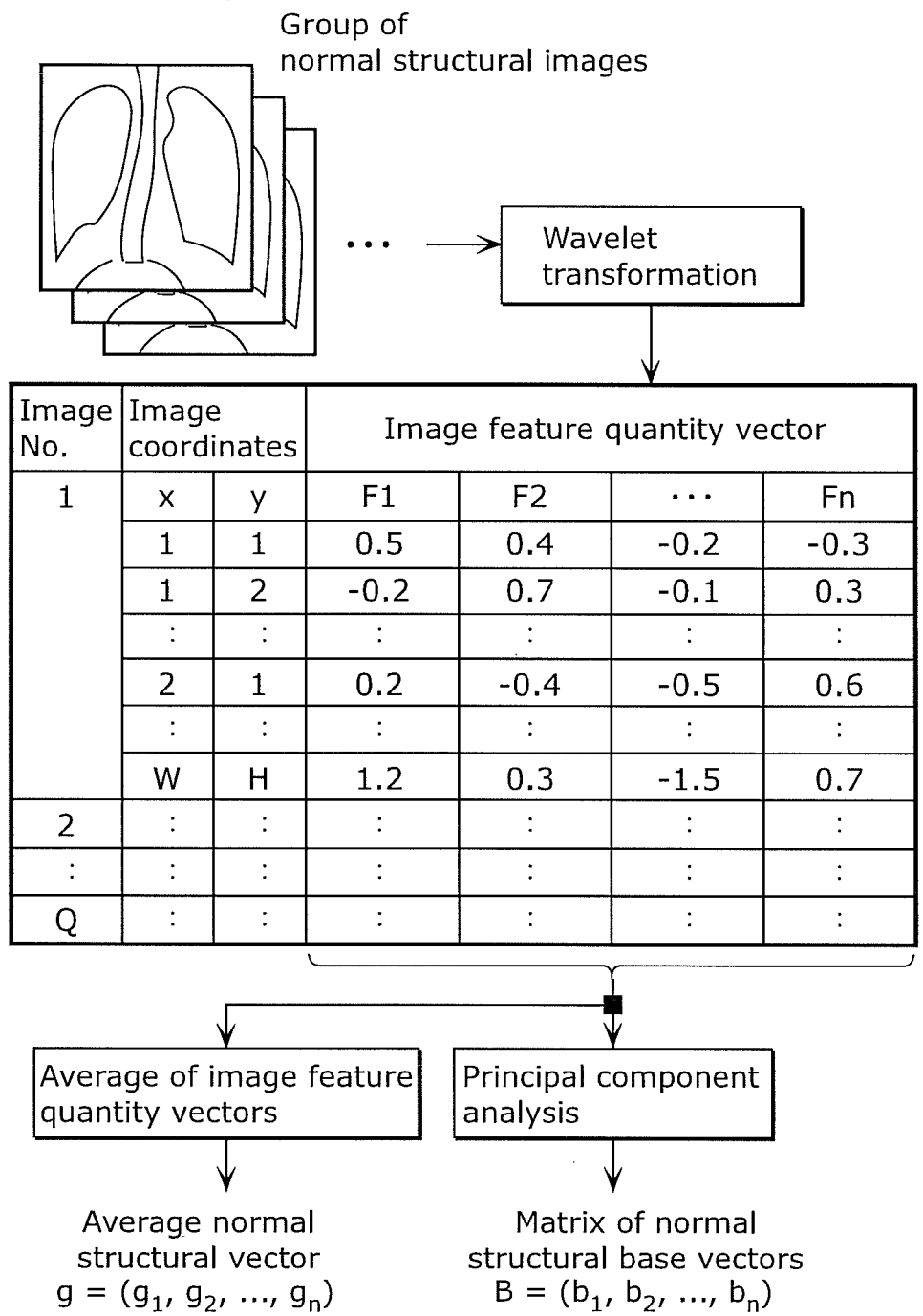
FIG. 5 is a diagram for explaining a method for calculating base vectors and an average vector for normal structures.

The normal structural base vector matrix B and the average normal structural vector g are calculated on the basis of the image feature quantity vectors calculated from a large number of normal structural images, as shown in FIG. 5. If, for example, W is the width of the normal structural images and H is the height of the normal structure images, (W×H) image feature quantity vectors are calculated from a single normal structural image. Assuming that Q is the number of normal structural images, (W×H×Q) image feature quantity vectors are obtained from Q normal structural images. The number of dimensions of each image feature quantity vector is assumed to be n.

The average normal structural vector g is obtained by calculating an average value for each element of the image feature quantity vectors.

The normal structural base vector matrix B is calculated through principal component analysis as eigen vectors $b_1$, $b_2$, ..., and $b_n$ that are solutions of simultaneous equations expressed by Expression 3 below.

$$Sb_1 = \lambda_1 b_1 \qquad \text{[Expression 3]}$$
$$Sb_2 = \lambda_2 b_2$$
$$\vdots$$
$$Sb_n = \lambda_n b_n$$

Here, a matrix S represents a variance-covariance matrix and is given by Expression 4 below.

$$S = \begin{pmatrix} s_1^2 & s_1 s_2 & \ldots & s_1 s_n \\ s_1 s_2 & s_2^2 & \ldots & s_2 s_n \\ \vdots & \vdots & \ddots & \vdots \\ s_1 s_n & s_2 s_n & \ldots & s_n^2 \end{pmatrix} \qquad \text{[Expression 4]}$$

where $s_i$ is the variance of i-dimensional elements of the image feature quantity vectors. Since the number of image feature quantity vectors obtained is (W×H×Q) as described above, there are (W×H×Q) i-dimensional elements of the image feature quantity vectors, and $s_i$ is the variance of these i-dimensional elements.

The eigen value λ is given by Expression 5 below.

$$\begin{vmatrix} s_1^2 - \lambda & s_1 s_2 & \cdots & s_1 s_n \\ s_1 s_2 & s_2^2 - \lambda & \cdots & s_2 s_n \\ \vdots & \vdots & \ddots & \vdots \\ s_1 s_n & s_2 s_n & \cdots & s_n^2 - \lambda \end{vmatrix} = 0 \qquad [\text{Expression 5}]$$

Here, n eigen values λ are obtained and are respectively denoted by $\lambda_1, \lambda_2, \ldots,$ and $\lambda_n$ in order of decreasing value.

Through the operations described above, the base representation unit 103 transforms the image feature quantity vectors (the test image feature quantity vectors $f_p$) of the test image to a base representation and generates the test coefficient vectors $\alpha_p$. This makes it possible to compare the test image with the normal structural images. The test coefficient vectors $\alpha_p$ output from the base representation unit 103 are input to the nearest neighbor vector detection unit 104 and the lesion determination unit 106, and are used for comparison with the normal structural images.

Note that the normal structural base vector matrix B and the average normal structural vector g that are necessary for the calculation of Expression 2 are calculated in advance and stored in the base representation unit 103. It is noted here that images including no abnormal findings are basically determined as normal structural images, but even images that include a lesion site in part can be samples to be used for calculation of the normal structural base vector matrix B and the average normal structural vector g if those images include no lesion site in their areas that are used to calculate the image feature quantities. In the case of FIG. 4, the four blocks including the block 34, the right adjacent block 35, the bottom adjacent block 36, and the lower-right adjacent block 37 are involved in the calculation of the image feature quantities. If these four blocks include no lesion site, this image can be a sample to be used for the calculation of the normal structural base vector matrix B and the average normal structural vector g. In this case, the lesion site can be separated from the normal structure by enclosing the lesion site by a line. In addition, if an area used to calculate the image feature quantities is controlled so as not to span the line enclosing the lesion site, the normal structural base vector matrix B and the average normal structural vector g can be accurately acquired. The method for inputting the line for enclosing a lesion site is not intended to be limited, and even if, for example, doctors draw lines with a mouse or the like during diagnosis, it would not be so much burdensome. There are also some cases in which medical phrases representing areas may be written in findings. In such a case, if data indicating the relationship between medical phrases and the positions in medical images is prepared in advance, it is possible to specify the position of a lesion site without having the manpower and to separate the lesion site from the normal structure.

Furthermore, past cases diagnosed as "having a lesion site" are referenced to calculate image feature quantity vectors for the lesion area in advance. If there are small differences between the image feature quantity vectors for the lesion site and the image feature quantity vectors for a target image for which it is desired to acquire a normal structure, it is highly possible that the target image includes a lesion site. Accordingly, if the distance between two vectors is smaller than a predetermined threshold value, the target image is not added to a group of normal structural images.

The nearest neighbor vector detection unit 104 is configured to detect a normal coefficient vectors α that is most similar to a test coefficient vector $\alpha_p$ from among the normal coefficient vectors α stored in the normal coefficient vector storage unit 105. The normal coefficient vectors α each have, as its vector elements, coefficients used to represent each of the image feature quantity vectors of the normal structural images as a linear combination of the base vectors calculated from these image feature quantity vectors.

The normal coefficient vectors α are calculated using Expression 6 below.

$$\alpha = B^{-1}(f - g) \qquad [\text{Expression 6}]$$

$$\Leftrightarrow \begin{pmatrix} \alpha_1 \\ \alpha_2 \\ \vdots \\ \alpha_n \end{pmatrix} = (b_1 \; b_2 \; \cdots \; b_n)^{-1}(f - g)$$

$$\Leftrightarrow \begin{pmatrix} \alpha_1 \\ \alpha_2 \\ \vdots \\ \alpha_n \end{pmatrix} = \begin{pmatrix} b_{1,1} & b_{2,1} & \cdots & b_{n,1} \\ b_{1,2} & b_{2,2} & \cdots & b_{n,2} \\ \vdots & \vdots & & \vdots \\ b_{1,n} & b_{2,n} & \cdots & b_{n,n} \end{pmatrix}^{-1} \begin{pmatrix} f_1 - g_1 \\ f_2 - g_2 \\ \vdots \\ f_n - g_n \end{pmatrix}$$

Here, vectors f are normal image feature quantity vectors. The normal image feature quantity vectors f are calculated similarly to the test image feature quantity vectors $f_p$, using a normal structural image instead of a test image. Expression 6 has the same structure as Expression 2 and calculates the normal coefficient vectors α, using the normal image feature quantity vectors f instead of the test image feature quantity vectors $f_p$ in Expression 2.

The normal coefficient vector storage unit 105 is configured to store the same number of normal coefficient vectors α as the number of normal structural images, the normal coefficient vectors α being the results of calculation of Expression 6.

The nearest neighbor vector detection unit 104 is configured to calculate the distance between each of the test coefficient vectors $\alpha_p$ and each of the normal coefficient vectors α and detect a nearest neighbor normal coefficient vector α that has the shortest distance. After having detected the nearest neighbor normal coefficient vector α, the nearest neighbor vector detection unit 104 transmits the detected nearest neighbor normal coefficient vector α, together with the distance between the two vectors, to the lesion determination unit 106.

The lesion determination unit 106 is configured to determine, for each pixel in the text image, the presence or absence of a lesion site on the basis of the distance between the test coefficient vector $\alpha_p$ and the normal coefficient vector α. In other words, the lesion determination unit 106 is configured to compare the distance between the test coefficient vector $\alpha_p$ and the normal coefficient vector α with a determination threshold value. If the calculated distance is greater than the determination threshold value, the lesion determination unit 106 determines the pixel of interest, from which the test coefficient vector $\alpha_p$ has been calculated, as a pixel in a lesion site, and if the distance is smaller than or equal to the determination threshold value, the lesion determination unit 106 determines the pixel of interest as a pixel in the normal site. Note that the determination threshold value used to determine the presence or absence of a lesion is calculated from past cases and is stored in advance in the first threshold value database 109.

Figure 6:
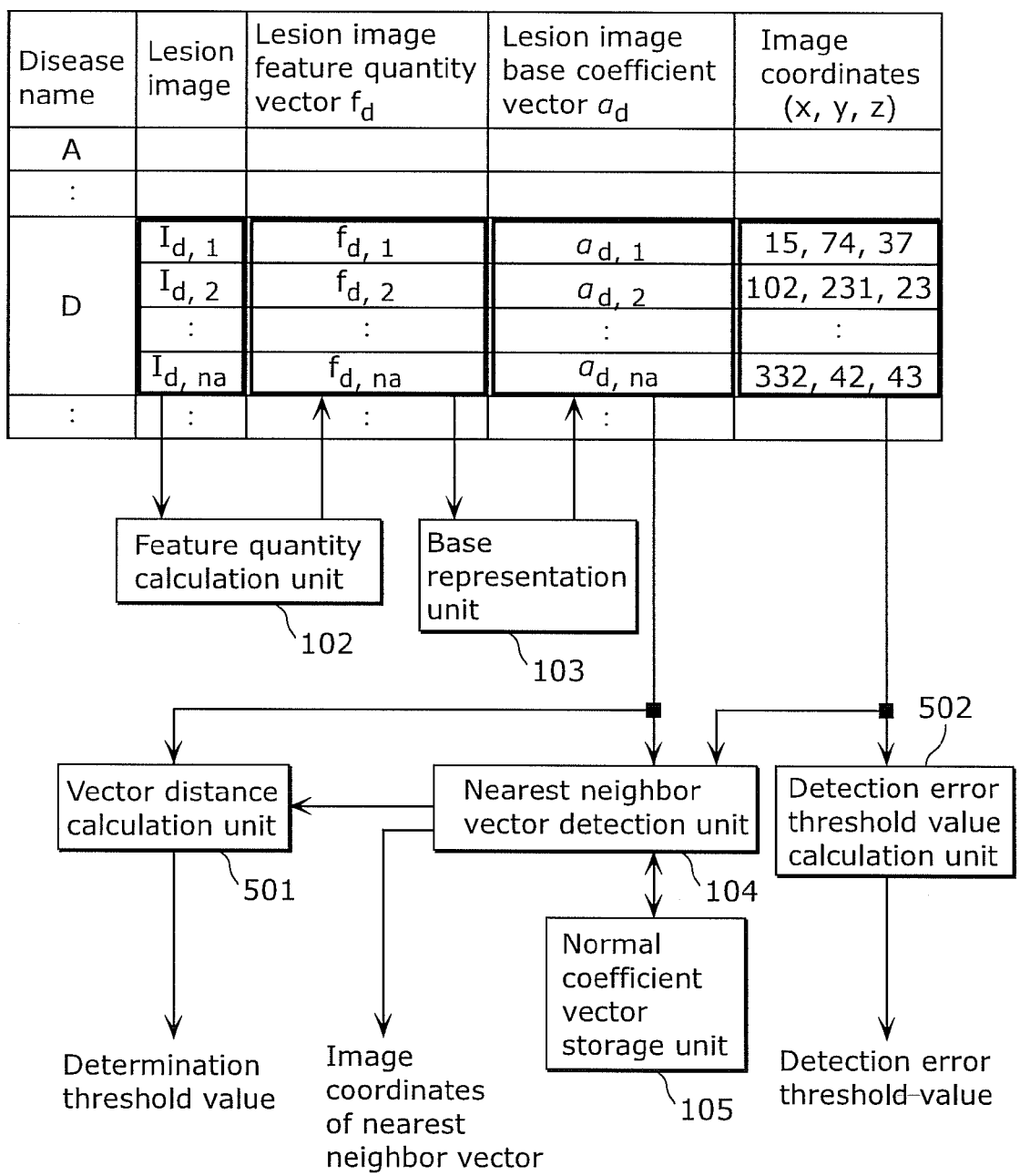
FIG. 6 is a diagram showing an example of the method for determining a determination threshold value used to determine the presence or absence of a lesion.

FIG. 6 shows an example of the method for determining the determination threshold value used to determine the presence or absence of a lesion. The determination threshold value is determined by a determination threshold value determination apparatus that includes the feature quantity calculation unit 102, the base representation unit 103, the nearest neighbor vector detection unit 104, the normal coefficient vector storage unit 105, a vector distance calculation unit 501, and a detection error threshold value calculation unit 502.

First, lesion images in which the presence of a lesion site has been confirmed are acquired from past cases and are classified by the disease name. Next, the feature quantity calculation unit 102 calculates, for example, a plurality of image feature quantities for each set of image coordinates (for each pixel) in a lesion image $I_d$ classified under a disease name D and generates a lesion image feature quantity vector $f_d$ ($f_{d,1}$ to $f_{d,na}$) having the calculated image feature quantities as its vector elements. The lesion image feature quantity vector $f_d$ is generated for each pixel. The base representation unit 103 substitutes the generated lesion image feature quantity vector $f_d$ into the vector $f_p$ of Expression 2 and transforms the lesion image feature quantity vector $f_d$ into a vector $\alpha_p$. This vector $\alpha_p$ serves as a lesion coefficient vector $\alpha_d$. Then, the nearest neighbor vector detection unit 104 detects a normal coefficient vector $\alpha$ that is most similar to the lesion coefficient vector $\alpha_d$ from among the normal coefficient vectors $\alpha$ stored in the normal coefficient vector storage unit 105. For example, a normal coefficient vector $\alpha$ having the shortest distance from the lesion coefficient vector $\alpha_d$ is detected. The vector distance calculation unit 501 calculates the distance between the detected nearest neighbor normal coefficient vector $\alpha$ and the lesion coefficient vector $\alpha_d$, and sets the calculated distance to a determination threshold value used to determine the presence or absence of a lesion. It is, however, noted that, for example, setting an average or median value of determination threshold values calculated from each pixel in each lesion site to a final determination threshold value is more appropriate because a large number of lesion images are classified under the same disease name.

The lesion determination unit 106 of the diagnostic support apparatus 100 further confirms the position of a pixel used to calculate each of the test coefficient vectors $\alpha_p$ and the normal coefficient vector $\alpha$ detected as the nearest neighbor vector, in order to avoid a detection error. As shown in FIG. 6, when the nearest neighbor normal coefficient vector $\alpha$ has been detected, the nearest neighbor vector detection unit 104 of the determination threshold value determination apparatus outputs the image coordinates of the nearest neighbor normal coefficient vector $\alpha$ as nearest neighbor vector image coordinates and stores the nearest neighbor vector image coordinates in the first threshold value database 109. In the case of a CT image, the image coordinates consist of a z-coordinate that indicates the slice location and x- and y-coordinates that indicate the position in the slicing plane. In the case of a plain radiographic image of the chest in which slicing is not performed, the z-coordinate can be fixed at 1, for example.

In the present embodiment, alignment is indirectly performed through the matching of the shift-invariant feature quantities. Thus, deformation processing such as directly deforming a plurality of normal structural images or a test image so that the corresponding points are placed at the same image coordinates is not performed. Accordingly, in most cases, the corresponding points in the normal structural images and the test image have different image coordinates as shown in FIG. 1. However, such differences in the image coordinates should fall within a certain degree of range, and accordingly the positions of the corresponding points are not so much far from each other. For example, in the case of a plain radiographic image of the chest, there are certain guidelines for image capturing methods, and images are captured in a situation where patients turn their bodies slightly within the range prescribed by the guidelines. In CT and MRI (magnetic resonance imaging), a patient lies on the bed and the relative positions of the patient and an imaging apparatus are fixed. CT images and MR images thus have smaller differences between image coordinates due to different shooting conditions than plain radiographic images of the chest. Meanwhile, patients have different shapes, and the image coordinates of corresponding points do not match when normal structural images and test images of different patients are compared. However, the image coordinates of the corresponding points are not considerably different from each other because the relative positions of the internal organs and bones, such as the relative positions of the lugs and the heart or the relative positions of the lungs and the shoulder blades, are the same among patients.

From the above point of view, the lesion determination unit 106 determines that a detection error has occurred, when the distance between the pixel used to calculate the test coefficient vector $\alpha_p$ and the pixel used to calculate the detected nearest neighbor normal coefficient vector $\alpha$ is greater than a predetermined detection error threshold value. When having determined that a detection error has occurred, the lesion determination unit 106 outputs a detection error notification signal 108 to the nearest neighbor vector detection unit 104 so as to instruct the nearest neighbor vector detection unit 104 to re-detect the nearest neighbor normal coefficient vector. Upon receipt of the detection error notification signal 108, the nearest neighbor vector detection unit 104 detects another nearest neighbor normal coefficient vector.

The detection error threshold value serving as a criterion for detecting a detection error is stored in the second threshold value database 110. The method for determining the detection error threshold value is not limited, and the detection error threshold value may be set for each disease name, for example. The image coordinates in a lesion site are obtained from past cases as shown in FIG. 6. Accordingly, the detection error threshold value calculation unit 502 calculates the distance between two sets of image coordinates that are most distant from each other in the distribution of image coordinates in all data for the disease name D, and determines the calculated distance as the detection error threshold value. Alternatively, the detection error threshold value calculation unit 502 may determine the distance between a center of the distribution of the image coordinates and a set of image coordinates that is most distant from the center as the detection error threshold value. The detection error threshold value calculation unit 502 may also roughly classify the position of each internal organ of a patient in accordance with the image coordinates (x, y, z) of the position, calculate the distance from a certain internal organ to another internal organ, and determine the calculated distance as the detection error threshold value.

In addition, the nearest neighbor vector detection unit 104 may detect a nearest neighbor normal coefficient vector from among a plurality of normal coefficient vectors $\alpha$ that correspond respectively to pixels located within a predetermined range of distances from a pixel to be processed (a target pixel). This makes it possible to shorten the time required for detection of the nearest neighbor normal coefficient vector. At the same time, it is also possible to reduce the occurrence of search errors. In other words, by limiting the range of reference for nearest neighbor vectors, it is possible to avoid a situation in which the image coordinates of corresponding points between the normal structural images and the test image are not so different as to exceed the sizes of the internal organs. It is thus sufficient that the nearest neighbor vector detection unit 104 references the normal coefficient vectors α of the pixels within a predetermined range of distances from the image coordinates of the test coefficient vector $α_p$. The method for setting the range of reference is not limited, and for example, the range of reference may be set using a maximum detection error threshold value stored in the second threshold value database 110 as the above predetermined distance. The second threshold value database 110 stores a detection error threshold value for each disease name, and the magnitudes of the stored detection error threshold values differ from disease name to disease name. Setting a maximum detection error threshold value to the above predetermined distance makes it possible to cope with any disease name. In this case, no lesion sites are left unnoticed even if the range of reference is limited. Note that, if the conditions for detection of a lesion site can be narrowed down on the basis of patient information other than the image information, such as clinical information or pre-existing conditions, it is possible to further limit the range of reference for normal coefficient vectors α in order to reduce the time required for detection of a lesion site as short as possible.

In the example of FIG. 6, lesion images are classified by the disease name. If lesion images can be classified by the condition of each disease with use of findings attached to the lesion images, a determination threshold value for determining the condition of the disease can be calculated. For example, lesion images of tumors are divided into two categories, namely those of benign tumors and those of malignant tumors, and a determination threshold value is obtained for each category of lesion images. The lesion determination unit 106 can use these two determination threshold values to determine the condition of the disease as to whether the tumor is benign or malignant.

Figure 7:
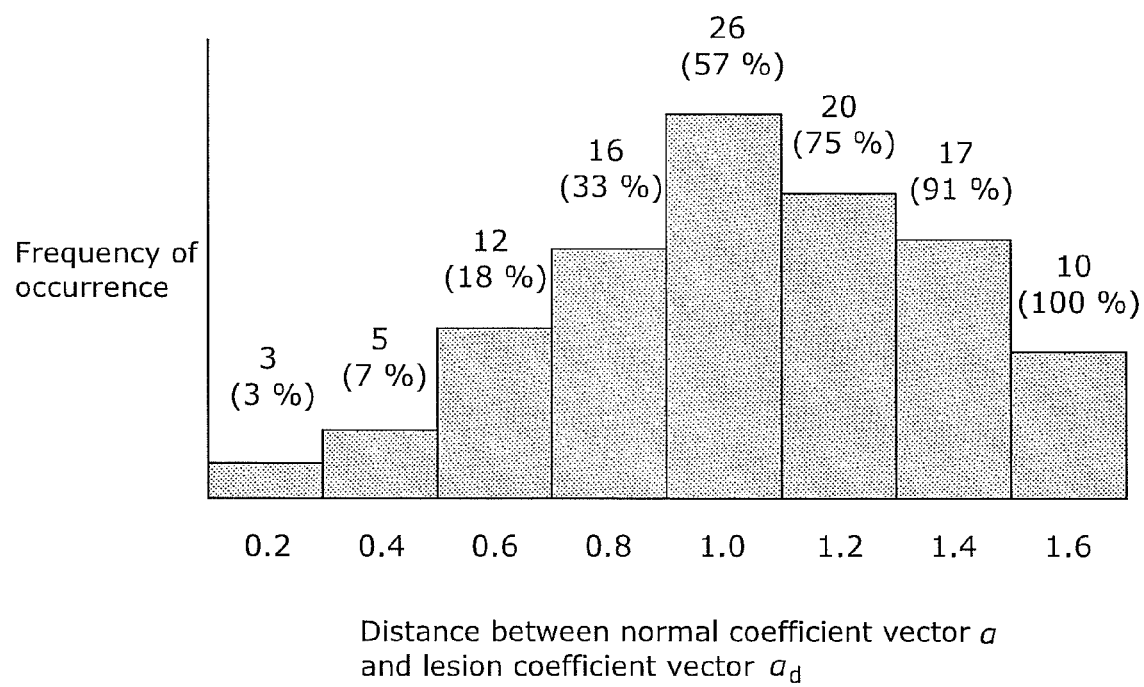
FIG. 7 is a histogram of distances between a lesion coefficient vector and a normal coefficient vector.

While the descriptions thus far have discussed a case in which the lesion determination unit 106 makes alternative determination such as the presence or absence of a lesion site, the lesion determination unit 106 can also calculate a value indicating the possibility of the presence of a lesion. FIG. 7 is a histogram of distances between the normal coefficient vector α and the lesion coefficient vector $α_d$ classified under the disease name D. The average and median values of distances are both 1.0, and in the case of alternative determination as to the presence or absence of a lesion site, the determination threshold value is set to 1.0. The percentages in parentheses written under the frequencies of occurrence indicate the ratios of cumulative frequencies of occurrence to the total frequency of occurrence. For example, if the distance between the normal coefficient vector α and the lesion coefficient vector $α_d$ is 1.0, the lesion determination unit 106 can determine that the possibility of the presence of a lesion site is 57%. The maximum distance is 1.6, and if the distance is 1.6, the lesion determination unit 106 can determine that the possibility of the presence of a lesion site is 100%.

The output unit 111 is configured to output the result of determination by the lesion determination unit 106.

The display unit 107 is configured by a display device or the like. The display unit 107 is configured to, upon receipt of the determination result indicating the presence of a lesion site from the output unit 111, replace pixel values at the image coordinates within the lesion site by a specific color (e.g., red or yellow) and display the presence and position of the lesion site as an image.

Figure 8:
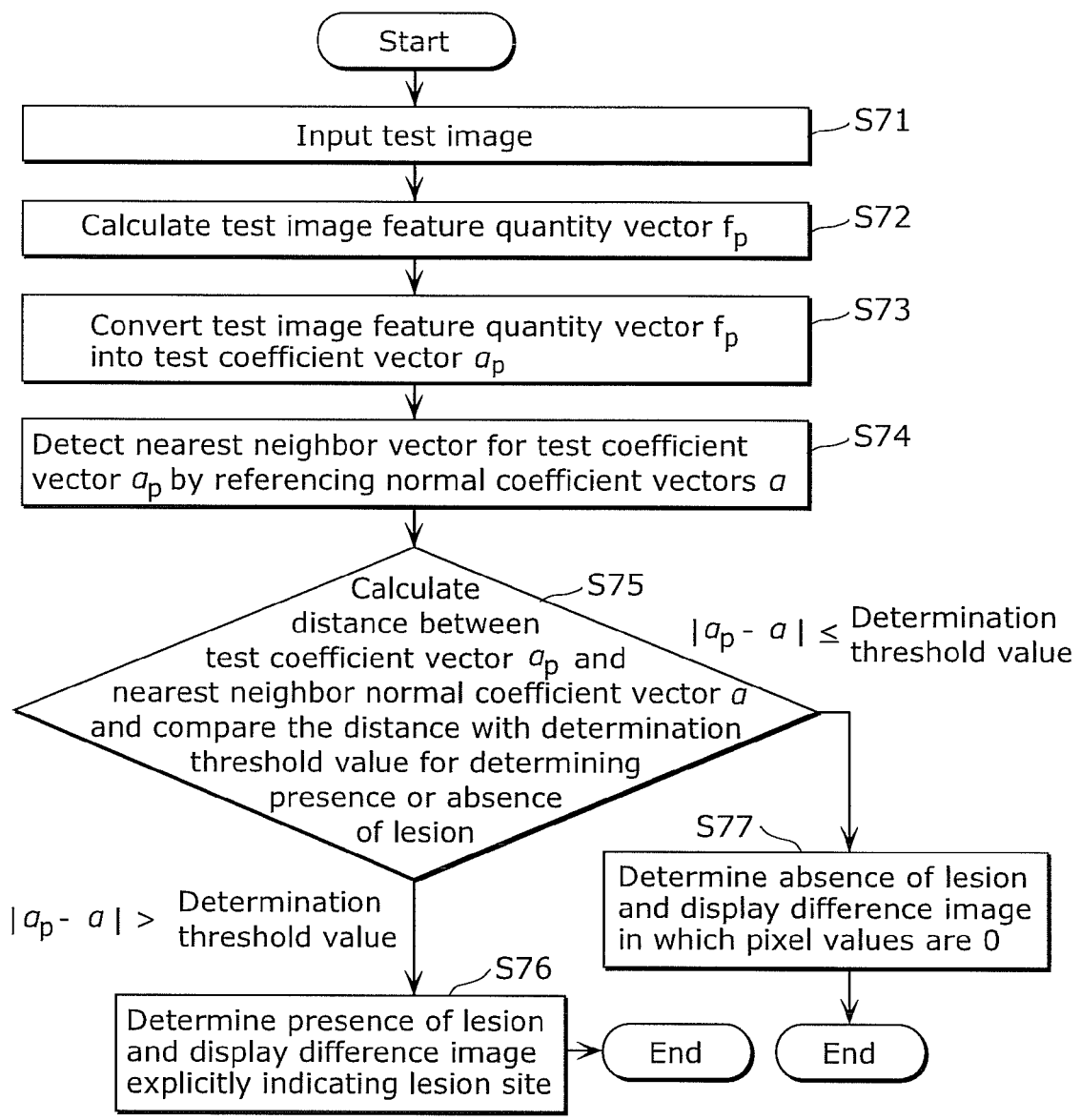
FIG. 8 is a flowchart of processing performed by the diagnostic support apparatus.

FIG. 8 is a flowchart of processing performed by the diagnostic support apparatus 100.

Prior to the processing of the diagnostic support apparatus 100, the normal coefficient vectors α are stored in the normal coefficient vector storage unit 105. Specifically, base vectors are calculated from a group of shift-invariant feature quantity vectors acquired from a plurality of normal structural images. Then, the normal coefficient vectors α are generated, each having, as its vector elements, coefficients used to represent each of the normal structural images as a linear combination of the base vectors. The generated normal coefficient vectors α are stored in the normal coefficient vector storage unit 105.

In step S71, the input unit 101 receives a test image.

In step S72, the feature quantity calculation unit 102 calculates a plurality of image feature quantities for each pixel in the test image received by the input unit 101. The feature quantity calculation unit 102 then generates, for each pixel in the test image, a test image feature quantity vector $f_p$ having the calculated image feature quantities as its vector elements, and outputs the generated test image feature quantity vectors $f_p$ to the base representation unit 103.

In step S73, the base representation unit 103 transforms, for each pixel in the test image, the test image feature quantity vector $f_p$ into a test coefficient vector $α_p$.

In step S74, the nearest neighbor vector detection unit 104 references the normal coefficient vectors α stored in the normal coefficient vector storage unit 105 and detects, for each pixel in the test image, a nearest neighbor normal coefficient vector α that is most similar to the test coefficient vector $α_p$.

In step S75, the lesion determination unit 106 calculates, for each pixel in the test image, a distance between the test coefficient vector $α_p$ and the nearest neighbor normal coefficient vector α and compares the calculated distance with a determination threshold value for determining the presence or absence of a lesion.

If the distance between the test coefficient vector $α_p$ and the nearest neighbor normal coefficient vector α is greater than the determination threshold value, the procedure proceeds to step S76. In step S76, the target pixel is determined as a "pixel including a lesion site," and the determination result is output to the output unit 111. Upon receipt of the determination result from the output unit 111, the display unit 107 gives a pixel value of 0 (black) at the position of the target pixel and displays a difference image that explicitly indicates the lesion site.

On the other hand, if the distance between the test coefficient vector $α_p$ and the nearest neighbor normal coefficient vector α is less than or equal to the determination threshold value, the procedure proceeds to step S77. In step S77, the target pixel is determined as a "pixel including no lesion site," and the determination result is output to the output unit 111. Upon receipt of the determination result from the output unit 111, the display unit 107 gives a pixel value of 1 (white) at the position of the target pixel and displays a difference image.

With the configuration described above, the diagnostic support apparatus 100 can detect a lesion site from the difference between the test image and the normal structural images. The present embodiment eliminates the need for an alignment process as a result of using the shift-invariant feature quantities and improves the efficiency and quality of diagnostic practices.

Embodiment 2

The present embodiment, similarly to Embodiment 1, describes a diagnostic support apparatus that implements vectorization of image information with use of shift-invariant feature quantities and eliminates the need to set corresponding points for alignment. In particular, the present embodiment describes a diagnostic support apparatus that can present similar cases of a lesion site by referencing findings information in cooperation with a similar case search server.

Figure 9:
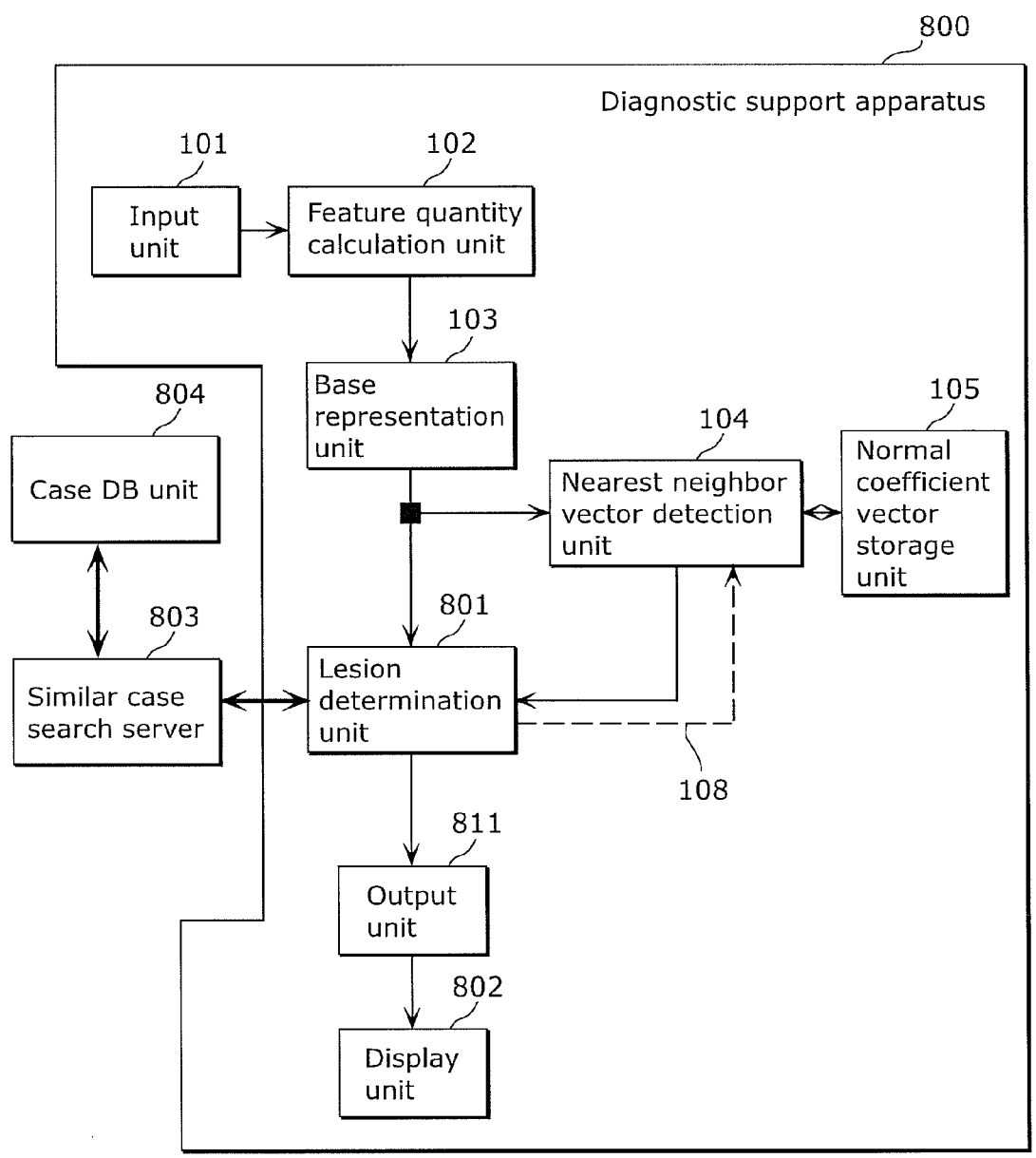
FIG. 9 is a block diagram showing a functional configuration of a diagnostic support apparatus according to Embodiment 2.

FIG. 9 is a block diagram showing a functional configuration of a diagnostic support apparatus 800 according to Embodiment 2. Note that constituent elements that are the same as those in FIG. 2 are denoted by the same reference numerals, and detailed descriptions thereof are not repeated.

The diagnostic support apparatus 800 includes the input unit 101, the feature quantity calculation unit 102, the base representation unit 103, the nearest neighbor vector detection unit 104, the normal coefficient vector storage unit 105, a lesion determination unit 801, an output unit 811, and a display unit 802.

The lesion determination unit 801, similarly to the lesion determination unit 106 of Embodiment 1, is configured to, for each pixel in a test image, determine the presence or absence of a lesion site on the basis of the distance between the test coefficient vector $\alpha_p$ and the normal coefficient vector $\alpha$.

The lesion determination unit 801 is connected to the similar case search server 803 and references diagnosed case data stored in a case database (DB) unit 804 via the similar case search server 803. Past case data refers to diagnostic results officially confirmed by doctors. The diagnostic support apparatus 800 is provided with the intension of supporting diagnosis by doctors or technicians and does not make final diagnostic determination. Past diagnostic results (past case data) are right answers for the diagnostic support apparatus 800 and accordingly absolute reference information. Meanwhile, doctors or technicians also make new diagnosis by referencing the past case data. In view of this, the efficiency and quality of diagnostic practices can further be improved if the diagnostic support apparatus 800 can present not only the presence or absence of a lesion but also the name of a disease and the condition of the disease.

From this point of view, the lesion determination unit 801 is configured to, when having determined the presence of a lesion in the test image, reference the case DB unit 804 via the similar case search server 803 and detect past case data similar to the lesion.

The output unit 811 is configured to output the determination result received from the lesion determination unit 801 and the past case data detected by the lesion determination unit 801.

The display unit 802 is configured by a display device or the like. The display unit 802, similarly to the display unit 107 of Embodiment 1, is configured to, upon receipt of the determination result and the similar case data from the output unit 811, display the presence and position of the lesion site as an image. In addition, the display unit 802 is also configured to display the past case data similar to the lesion site.

Figure 10:
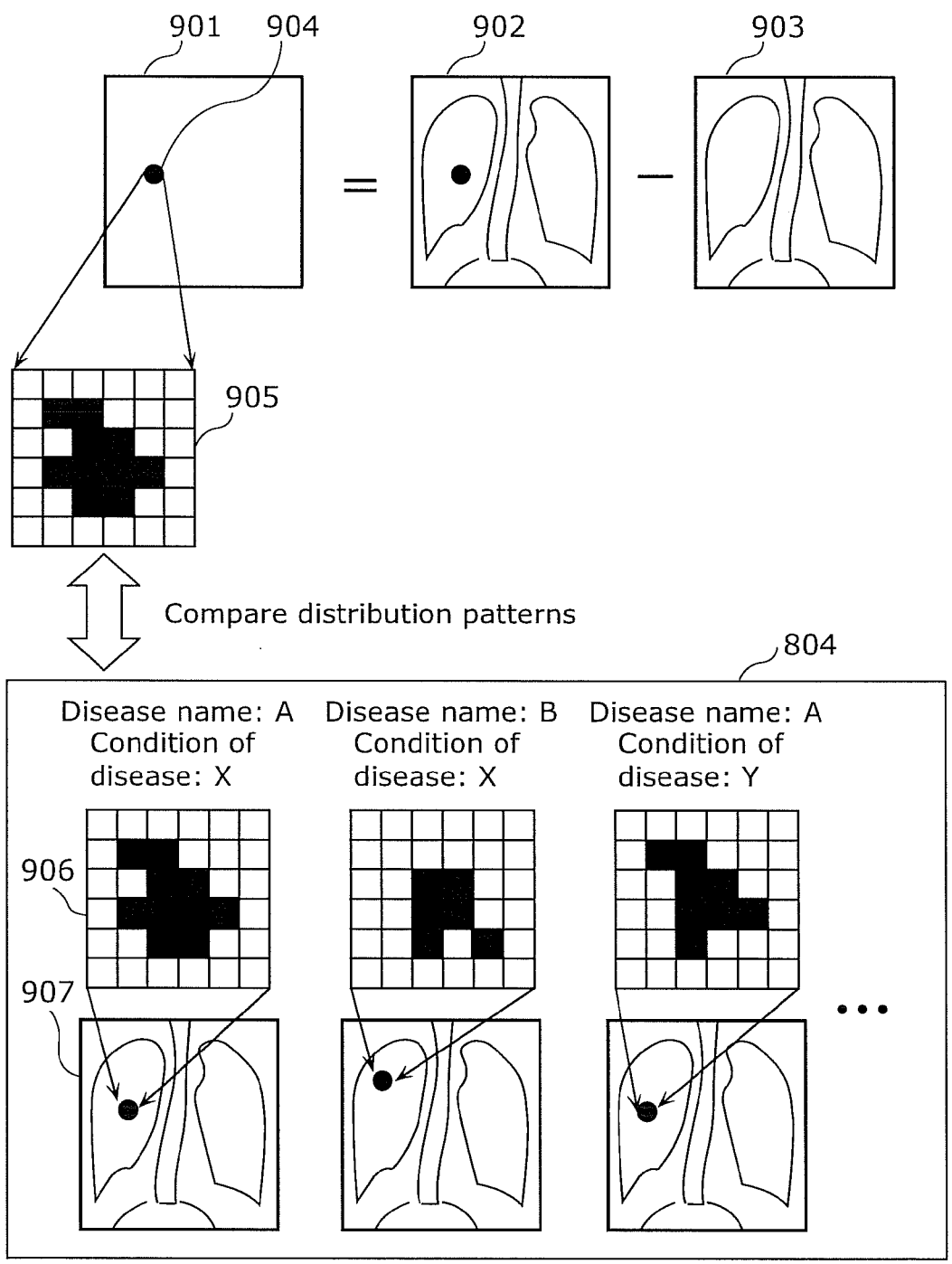
FIG. 10 is a diagram for explaining an example of a method for searching for similar case data, using a similar case search server.

FIG. 10 is a diagram for explaining an example of the method of search for similar case data, using the similar case search server 803.

The lesion determination unit 801 determines the difference between a test image 902 and a normal structural image 903. The determination result is expressed as a difference image 901. Here, the difference image 901 is an image in which the lesion site is indicated by pixel values of 0 (black) and the normal site is indicated by pixel values of 1 (white). Enlarging a lesion site 904 gives a distribution pattern 905. The distribution pattern 905 consists of pixels in the lesion site and pixels in the normal site. While the determination of either the lesion site or the normal site is made per pixel by the lesion determination unit 801, these determination results when viewed as an image can be considered as a pattern consisting of a plurality of pixels. It is highly likely that there is a correlation between the distribution pattern 905 and the determination of a disease name or the condition of the disease. Accordingly, the similar case search server 803 can use the distribution pattern 905 as a cue to extract similar case data including a similar distribution pattern 906 from the case DB unit 804.

In the case of FIG. 10, the similar case search server 803 detects an image 907 that includes a similar distribution pattern 906 most similar to the distribution pattern 905, and information attached to the image 907 such as a disease name, the condition of the disease, findings, and clinical data from among the case data stored in the case DB unit 804. For example, the disease name attached to the image 907 is A, and the condition of the disease is X.

Figure 11:
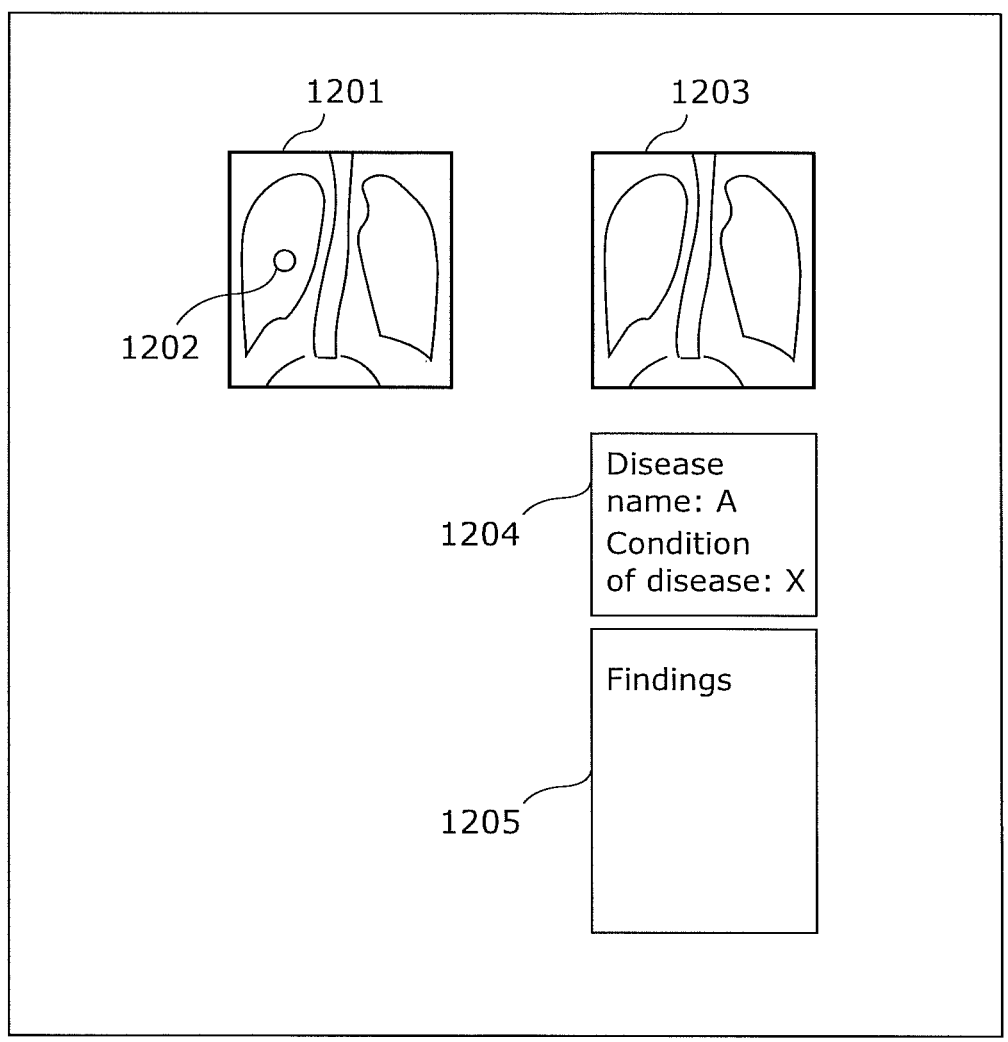
FIG. 11 shows an example of a determination result and similar case data displayed on a display unit.

FIG. 11 shows an example of the determination result and the similar case data displayed on the display unit 802. The display unit 802 displays an image 1201, an image 1203, a disease name/condition 1204, and findings 1205. The image 1201 is an image in which the lesion site in the test image 902 is enclosed by a line 1202. The image 1203 is the same as the image 907 shown in FIG. 10 and detected by the similar case search server 803. Note that the case DB unit 804 stores cases images such as the image 1203 for each disease name and each condition of the disease. According to this classification, the display unit 802 displays the fact that the disease name is A and the condition of the disease is X. Each case data is also accompanied with findings, and the findings 1205 for the image 1203 are displayed in this case.

Note that the present embodiment does not limit the method for determining whether or not distribution patterns are similar and the method for searching for a similar distribution pattern. For example, pattern matching between distribution patterns may be performed to determine whether or not the distribution patterns are similar and to specify the position of a similar distribution pattern in the image. Instead of the pattern matching, image feature quantities may be calculated from and compared between distribution patterns.

With the configuration described above, the diagnostic support apparatus 800 can detect a lesion site from the difference between a test image and normal structural images. According to the present embodiment, it is possible to present case data similar to a lesion site to a user by referencing the past case data. This improves the efficiency and quality of operations of diagnosing a disease and identifying the condition of the disease by doctors.

Embodiment 3

The present embodiment, similarly to Embodiments 1 and 2, describes a diagnostic support apparatus that implements vectorization of image information with use of shift-invariant feature quantities and eliminates the need to set corresponding points for alignment. In particular, the present embodiment eliminates the need to install an input device, a display device, an electronic patient record server, and a diagnostic support server at the same place.

Figure 12:
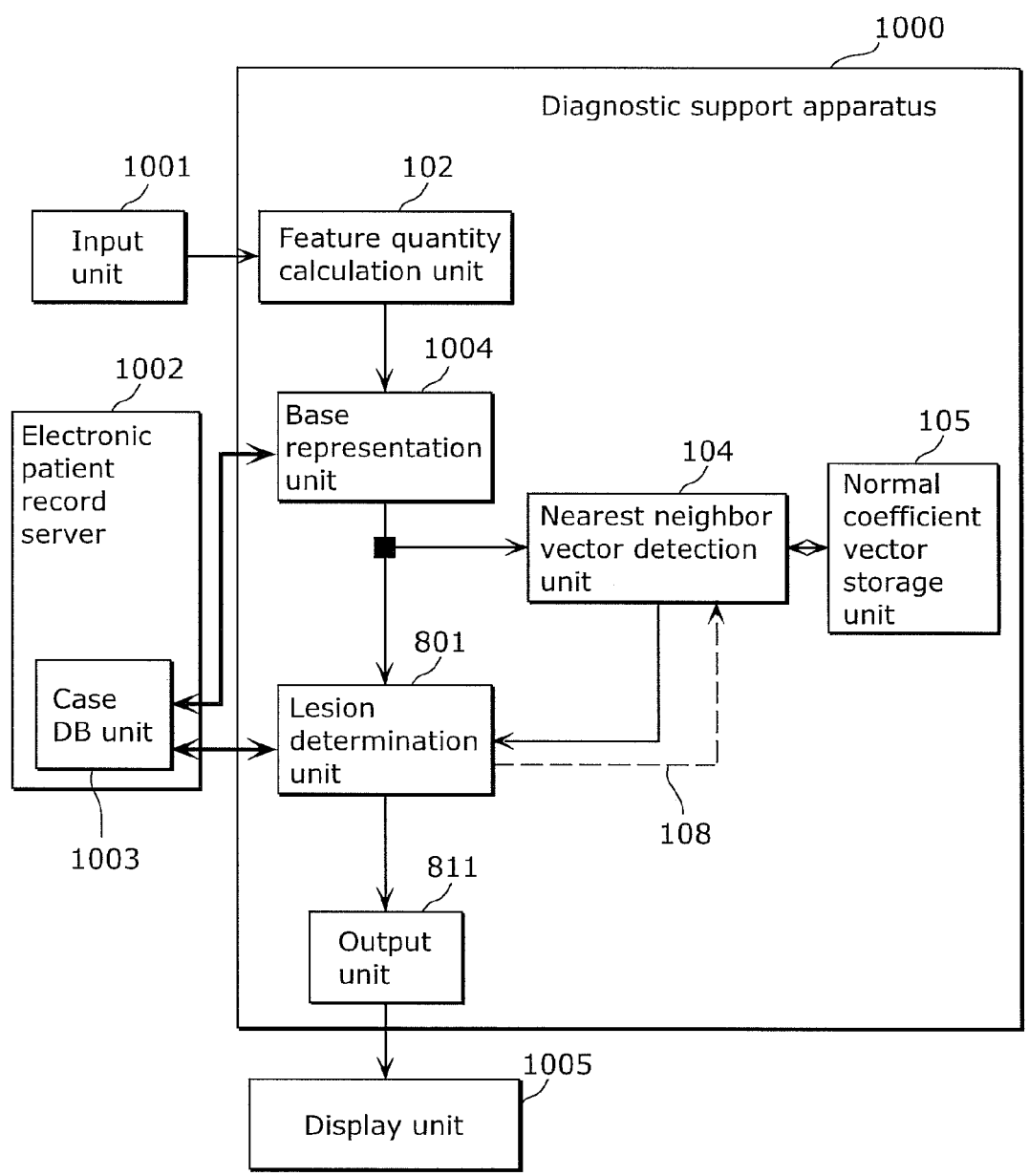
FIG. 12 is a block diagram showing a functional configuration of a diagnostic support apparatus according to Embodiment 3.

FIG. 12 is a block diagram showing a functional configuration of a diagnostic support apparatus 1000 according to Embodiment 3. Note that constituent elements that are the same as those in FIG. 2 or 9 are denoted by the same reference numerals, and detailed descriptions thereof are not repeated.

The diagnostic support apparatus 1000 includes the feature quantity calculation unit 102, a base representation unit 1004, the nearest neighbor vector detection unit 104, the normal coefficient vector storage unit 105, the lesion determination unit 801, and the output unit 811.

The feature quantity calculation unit 102 of the diagnostic support apparatus 1000 receives a test image from an input device 1001 via a network. The lesion determination unit 801 and the base representation unit 1004 are connected to an electronic patient record server 1002 via the network and reference past case data stored in a case DB unit 1003 of the electronic patient record server 1002. A difference image between the test image and normal structural images and similar case data, which are output from the lesion determination unit 801, are transmitted via the network to a display device 1005.

The input device 1001, the electronic patient record server 1002, and the display device 1005 are connected to the diagnostic support apparatus 1000 via a standard interface (e.g., a digital imaging and communication in medicine (DICOM) interface or a health level seven (HL7) interface). This allows the diagnostic support apparatus 1000 to receive a test image in various modalities and detect a lesion by referencing past case data. The diagnostic support apparatus 1000 can thus support the detection of a lesion by doctors or technicians.

The base representation unit 1004 acquires normal structural images from the case DB unit 1003. Normal structural images are added everyday because image-based diagnosis is carried out every day in hospitals. By acquiring a greater number of normal structural images to generate the normal structural base vector matrix B and the average normal structural vector g, it is possible to cope with various types of patient shapes and different shooting conditions. This increases the utility value of the diagnostic support apparatus 1000. It is thus desirable that the normal structural base vector matrix B and the average normal structural vector g be updated at any time. By connecting the lesion determination unit 801 to the electronic patient record server 1002, it is possible to reflect the updating of case data in the case DB unit 1003 and to detect similar case data from among past case data that includes the latest case data. Accordingly, the diagnostic support apparatus 1000 can more accurately support diagnosis.

With the configuration described above, the diagnostic support apparatus 1000 can support diagnosis without the input device 1001, the display device 1005, the electronic patient record server 1002, and the diagnostic support server being installed at the same place. With this apparatus, such diagnosis is possible in which a technician captures a test image and an image-based diagnostician at a distant location makes diagnosis while viewing the image of a lesion site and past case data similar to the lesion site displayed on the display device 1005.

Embodiment 4

The present embodiment, similarly to Embodiments 1 to 3, describes a diagnostic support apparatus that implement vectorization of image information with use of shift-invariant feature quantities and eliminates the need to set corresponding points for alignment. In particular, in the present embodiment, the possibility of the presence of a lesion site is presented using a plurality of presentation methods. This allows the diagnostic support apparatus to provide versatile diagnostic support.

Figure 13:
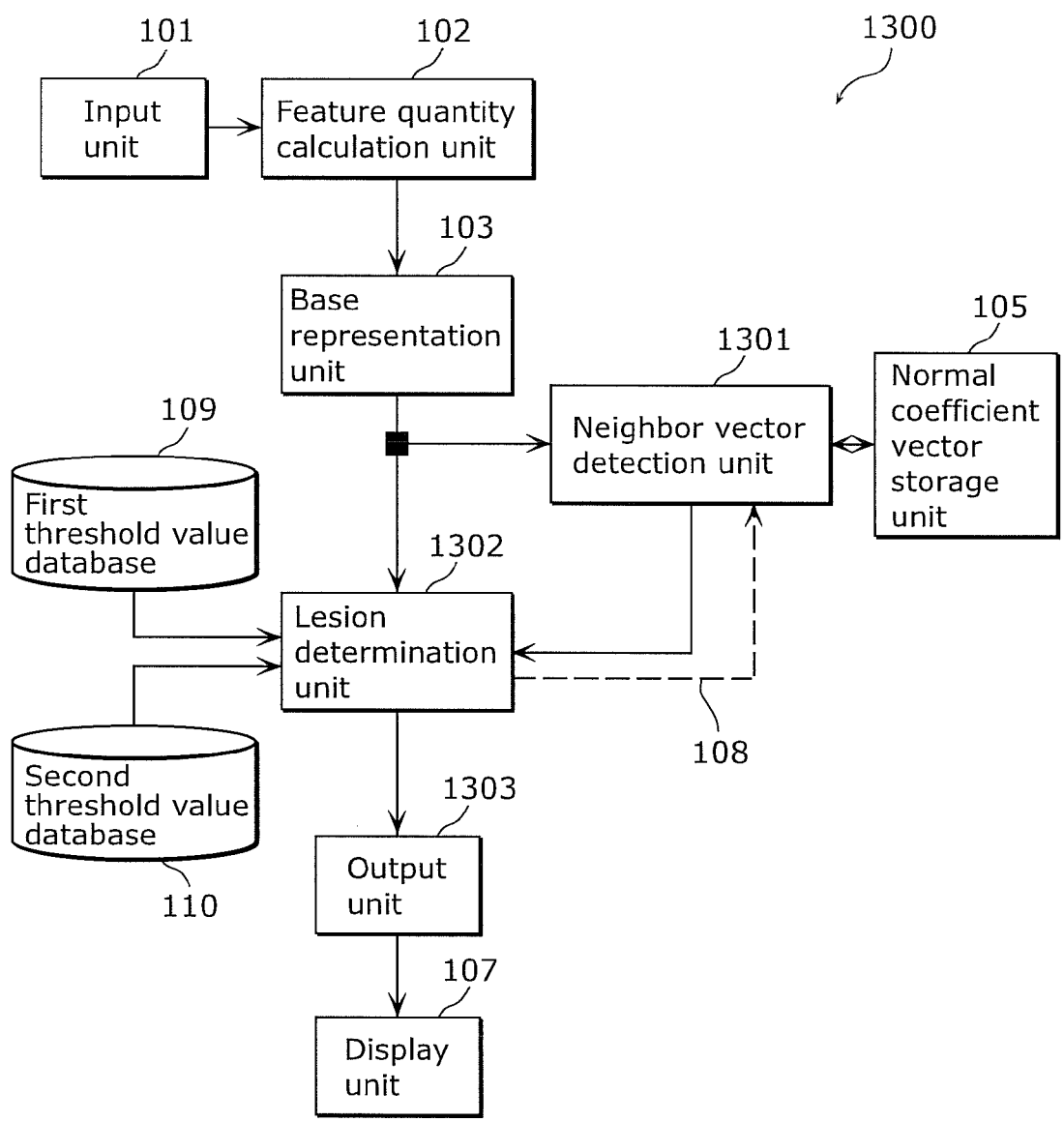
FIG. 13 is a block diagram showing a functional configuration of a diagnostic support apparatus according to Embodiment 4.

FIG. 13 is a block diagram showing a functional configuration of a diagnostic support apparatus according to Embodiment 4. Note that constituent elements that are the same as those in FIG. 2 are denoted by the same reference numerals, and detailed descriptions thereof are not repeated.

A diagnostic support apparatus 1300 includes the input unit 101, the feature quantity calculation unit 102, the base representation unit 103, a neighbor vector detection unit 1301, the normal coefficient vector storage unit 105, a lesion determination unit 1302, an output unit 1303, and the display unit 107.

The neighbor vector detection unit 1301 is configured to detect a plurality of normal coefficient vectors α that are similar to a test coefficient vector $α_p$ from among the normal coefficient vectors α stored in the normal coefficient vector storage unit 105. For example, three normal coefficient vectors α are detected in order of increasing distance with the test coefficient vector $α_p$.

The lesion determination unit 1302 is configured to receive the plurality of (e.g., three) normal coefficient vectors α detected by the neighbor vector detection unit 1301 and compare, for each of the received normal coefficient vectors α, the distance between the test coefficient vector $α_p$ and the normal coefficient vector α with a determination threshold value. On the basis of the comparison result, the lesion determination unit 1302, similarly to the lesion determination unit 106 of Embodiment 1, determines whether or not the pixel of interest from which the test coefficient vector $α_p$ has been calculated is a pixel in the lesion site.

The output unit 1303 is configured to classify the determination results from the lesion determination unit 106 for each of the normal coefficient vectors α and output the classification result to the display unit 107.

Figure 14:
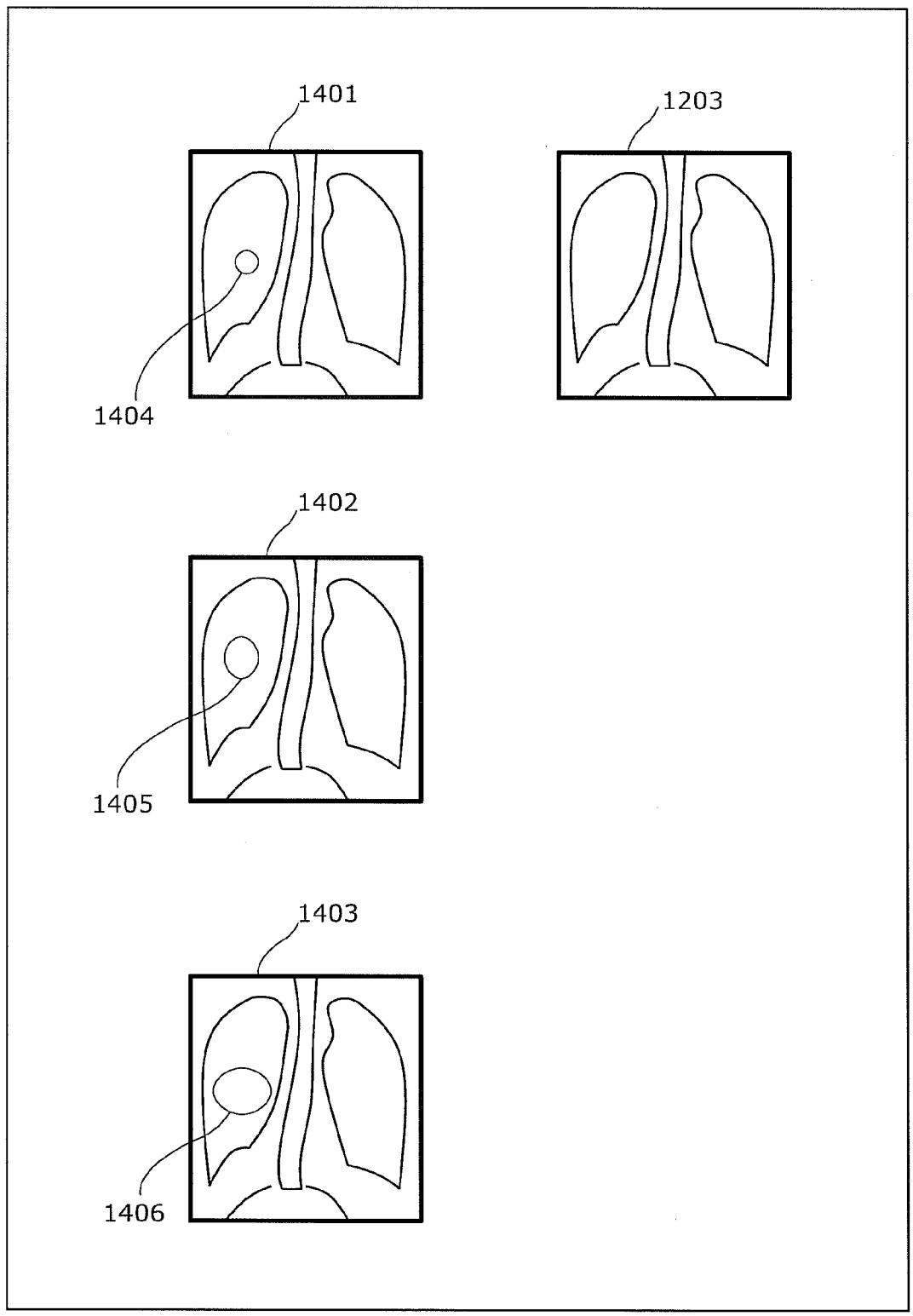
FIG. 14 shows an example of a determination result displayed on the display unit.

FIG. 14 shows an example of the determination results displayed on the display unit 107. As shown in FIG. 14, the display unit 107 displays a plurality of (e.g., three) determination results. For example, images 1401 to 1403 that indicate the determination results corresponding to an image 1203 serving as a test image are displayed. The image 1203 and the images 1401 to 1403 are the same test image, but in the images 1401 to 1403, lesion sites 1404 to 1406 are enclosed by lines. Specifically, the image 1401 shows the lesion site 1404 determined on the basis of the distance between the test coefficient vector $α_p$ and the normal coefficient vector α that is most similar to the test coefficient vector $α_p$. The image 1402 shows the lesion site 1405 determined on the basis of the distance between the test coefficient vector $α_p$ and the normal coefficient vector α that is second most similar to the test coefficient vector $α_p$. The image 1403 shows the lesion site 1406 determined on the basis of the distance between the test coefficient vector $α_p$ and the normal coefficient vector α that is third most similar to the test coefficient vector $α_p$. As the distance between the test coefficient vector $α_p$ and the normal coefficient vector α increases, the possibility that the image includes a lesion site increases. Thus, among the images 1401 to 1403, the image 1403 has the lesion site 1406 of the largest area. In other words, it can be said that a lesion site is detected more leniently in the image 1403 than in images 1401 and 1402. On the contrary, it can be said that a lesion site is detected more strictly in the image 1401 than in the images 1402 and 1403.

Medical interpretations of diseases and the conditions of disease are making steady progress. In particular, conferences held with participation of doctors and technicians become forums for new diagnostic methods and criteria based on cases that increase day by day. Presenting the determination results based on a plurality of lesion determination criteria as shown in FIG. 14 in such forums can be precious data for finding new interpretation.

As described above, Embodiments 1 to 4 described above that implement vectorization of image information with use of shift-invariant feature quantities do not require the setting of corresponding points for alignment. Accordingly, it is possible to generate normal structural images with stability and efficiency. In addition, the results of comparison between a test image and normal structural images based on the image-based diagnosticians' memories are converted into data format and can be used to objectively support diagnosis by image-based diagnosticians. The diagnostic results can be used in various scenes such as in the scene of informed consent and in the scenes of medical education and basic medicine.

Moreover, a lesion site can be detected with efficiency and accuracy. Image-based diagnosticians make new tests while referencing past case data that is updated day by day. Thus, the detection of a lesion with a calculator improves the work efficiency of image-based diagnosticians and facilitates a medical workflow. The confirmation of a disease name and the condition of the disease has significant influences on the determination of a treatment plan. Accordingly, diagnostic support by the diagnostic support apparatuses can contribute to improvements in the efficiency and quality of the entire medical field.

While the above has been a description of the diagnostic support apparatuses according to embodiments of the present disclosure, the present disclosure is not limited to these embodiments.

For example, the diagnostic support apparatuses may be implemented by a computer.

Figure 15:
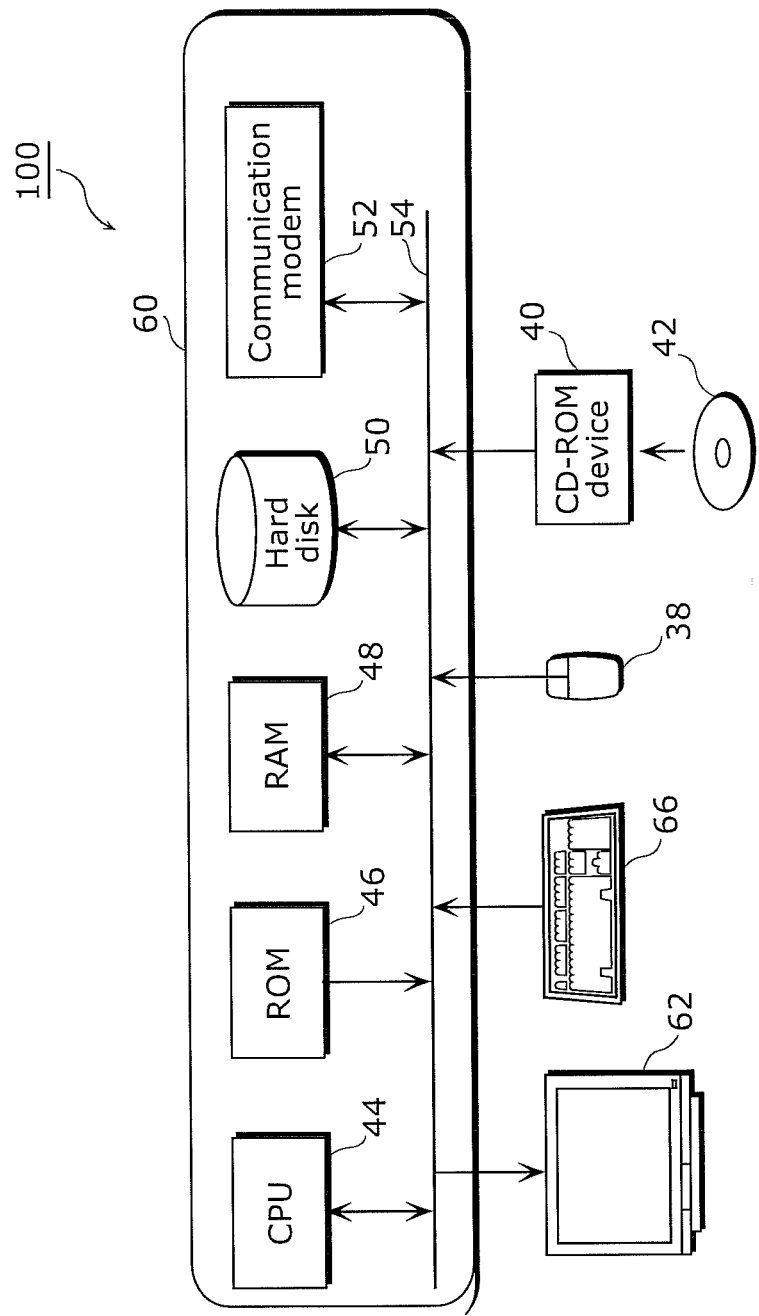
FIG. 15 is a block diagram showing a hardware configuration of a computer system that implements a diagnostic support apparatus.

FIG. 15 is a block diagram showing a hardware configuration of a computer system that implements the diagnostic support apparatus 100. Similarly to the diagnostic support apparatus 100, the diagnostic support apparatuses 800 and 1000 can also be implemented by a computer system.

The diagnostic support apparatus 100 includes a computer 60, a keyboard 66 and a mouse 38 for giving instructions to the computer 60, a display 62 for presenting information such as calculation results received from the computer 60, a compact disc-read only memory (CD-ROM) apparatus 40 for reading a program executed by the computer 60, and a communication modem (not shown).

Programs serving as processing performed by the diagnostic support apparatus 100 are stored in the CD-ROM 42 serving as a computer-readable recording medium and are read out by the CD-ROM device 40. The programs are also read by a communication modem 52 via a computer network.

The computer 60 includes a central processing unit (CPU) 44, a read-only memory (ROM) 46, a random access memory (RAM) 48, a hard disk 50, the communication modem 52, and a bus 54.

The CPU 44 executes the program read through the CD-ROM device 40 or the communication modem 52. The ROM 46 stores programs or data necessary for the operations of the computer 60. The RAM 48 stores data such as parameters at the time of execution of the program. The hard disk 50 stores programs and data, for example. The communication modem 52 communicates with other computers via the computer network. The bus 54 provides mutual connections of the CPU 44, the ROM 46, the RAM 48, the hard disk 50, the communication modem 52, the display 62, the keyboard 66, the mouse 38, and the CD-ROM device 40.

Some or all of the constituent elements of the above-described apparatuses may be configured by a single system large-scale integration (LSI). The system LSI is a super-multi-function LSI manufactured by integrating a plurality of constituent units on a single chip, and it is specifically a computer system configured by, for example, a microprocessor, a ROM, and a RAM. The RAM stores computer programs. The system LSI implements its function by the microprocessor operating in accordance with computer programs.

Some or all of the constituent elements of the above-described apparatuses may be configured as an IC card attachable to and detachable from the apparatuses or as a stand-alone module. The IC card or the module is a computer system configured by, for example, a microprocessor, a ROM, and a RAM. The IC card or the module may include the aforementioned super-multi-function LSI. The IC card or the module implements its function by the microprocessor operating in accordance with computer programs. The IC card or the module may be tamper-resistant.

The present disclosure may be implemented as any of the methods described above. In addition, the present disclosure may be a computer program for causing a computer to implement those methods or may be digital signals of the computer programs.

Furthermore, the present disclosure may be implemented as a non-transitory computer-readable recording medium having the computer programs or the digital signals recorded thereon. Examples of the recording medium include a flexible disc, a hard disk, a CD-ROM, an MO, a DVD, a DVD-ROM, a DVD-RAM, a Blu-ray (registered trademark) disc (BD), and a semiconductor memory. In addition, the present disclosure may be implemented as the digital signals recorded on any of the above non-transitory computer-readable recording medium.

The present disclosure may also be implemented as the aforementioned computer programs or digital signals transmitted via a telecommunication line, a wireless or wired communication line, a network represented by the Internet, a data broadcast, and so on.

The present disclosure may also be implemented as a computer system including a microprocessor and a memory, in which the memory stores the aforementioned computer programs and the microprocessor operates in accordance with the computer programs.

The present disclosure may also be implemented as another independent computer system by transmitting the aforementioned computer programs or digital signals recorded on the aforementioned non-transitory computer-readable recording media, or by transmitting these programs or digital signals via the aforementioned network or the like.

The above-described embodiments and variations may be combined arbitrarily.

Figure 16:
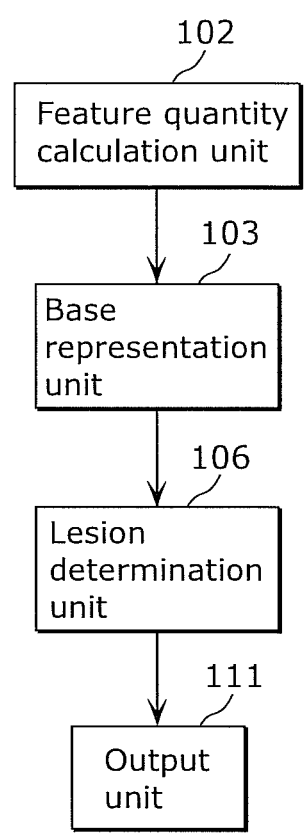
FIG. 16 shows essential constituent elements of a diagnostic support apparatus according to one or more exemplary embodiments.

It is noted that essential constituent elements of the diagnostic support apparatuses according to the present disclosure are the feature quantity calculation unit 102, the base representation unit 103, the lesion determination unit 106, and the output unit 111, as shown in FIG. 16. The details of those constituent elements are as described in Embodiment 1. The other constituent elements are desirably provided in the configuration, but are not an absolute necessity to implement the present disclosure.

The subject matter disclosed herein is to be considered descriptive and illustrative only, and the appended claims are of a scope intended to cover and encompass not only the particular embodiments disclosed, but also equivalent structures, methods, and/or uses.

Each of the structural elements in each of the above-described embodiments may be configured in the form of an exclusive hardware product, or may be realized by executing a software program suitable for the structural element. Each of the structural elements may be realized by means of a program executing unit, such as a CPU and a processor, reading and executing the software program recorded on a recording medium such as a hard disk or a semiconductor memory. Here, the software program for realizing a diagnostic support apparatus according to each of the embodiments is a program described below.

The program causes a computer to execute a diagnostic support apparatus according to each of the embodiments.

The diagnostic support apparatus according to one or more exemplary embodiments disclosed herein is applicable to, for example, a diagnostic support apparatus that supports image-based diagnosis by doctors by specifying a lesion site from a medical image.

The invention claimed is:

1. A diagnostic support apparatus comprising:
a non-transitory memory that stores a program; and
a hardware processor that executes the program and causes the diagnostic support apparatus to operate as:
a feature quantity calculation unit configured to vectorize a test image into shift-invariant feature quantities, the test image being an image in which presence of a lesion site is unknown;
a base representation unit configured to transform the shift-invariant feature quantities of the test image into a linear combination of base vectors with first coefficients, the base vectors being represented by eigen vectors calculated through principal component analysis of a plurality of vectors representing shift-invariant feature quantities of a plurality of normal structural images that include no lesion site;
a storage unit in which second coefficients are stored, the second coefficients being used to transform shift-invariant feature quantities calculated from one of the plurality of normal structural images into a linear combination of the base vectors;
a lesion determination unit configured to determine that the test image includes a lesion site when a difference between the first coefficients obtained from a result of the transforming by the base representation unit and the second coefficients stored in the storage unit is greater than a determination threshold value; and
an output unit configured to output a result of the determination by the lesion determination unit.

2. The diagnostic support apparatus according to claim 1, wherein the feature quantity calculation unit is configured to calculate a plurality of shift-invariant feature quantities from a pixel of interest in the test image and calculate a test image feature quantity vector having the calculated shift-invariant feature quantities as vector elements,
the base representation unit is configured to calculate the first coefficients and calculate a test coefficient vector having the calculated first coefficients as vector elements, the first coefficients being used to represent the test image feature quantity vector as the linear combination of the base vectors, the base vectors being calculated from a plurality of image feature quantity vectors each having, as vector elements, shift-invariant feature quantities calculated from pixels in each of the normal structural images, the normal structural images each being a medical image of a normal structure,
the diagnostic support apparatus further comprising
a nearest neighbor vector detection unit configured to detect a normal coefficient vector that is most similar to the test coefficient vector as a nearest neighbor vector from among a plurality of normal coefficient vectors each having second coefficients as vector elements, the second coefficients being used to represent each of the image feature quantity vectors as a linear combination of the base vectors, and
the lesion determination unit is configured to compare a distance between the test coefficient vector and the nearest neighbor vector with the determination threshold value, determine that the pixel of interest is in the lesion site when the distance is greater than the determination threshold value, and determine that the pixel of interest is in a normal site when the distance is smaller than or equal to the determination threshold value.

3. The diagnostic support apparatus according to claim 2, wherein the shift-invariant feature quantities are ones of wavelet coefficients, higher order local auto correlation (HLAC) feature quantities, scale invariant feature transform (SIFT) feature quantities, and histograms of oriented gradients (HOG) feature quantities.

4. The diagnostic support apparatus according to claim 2, wherein the medical image is one of a radiological image, an ultrasound image, and a pathological specimen image.

5. The diagnostic support apparatus according to claim 2, wherein the nearest neighbor vector detection unit is configured to detect, as the nearest neighbor vector, a normal coefficient vector that is most similar to the test coefficient vector from among a plurality of normal coefficient vectors corresponding to a plurality of pixels in the normal structural images, the pixels being located within a predetermined range of distances from the pixel of interest.

6. The diagnostic support apparatus according to claim 2, wherein the determination threshold value is either an average or median value of distances between a lesion coefficient vector and a nearest neighbor vector that is most similar to the lesion coefficient vector among the normal coefficient vectors, the lesion coefficient vector having, as vector elements, coefficients with which a lesion image feature quantity vector is represented as a linear combination of the base vectors, the lesion image feature quantity vector having, as vector elements, shift-invariant feature quantities calculated from a pixel in a lesion site.

7. The diagnostic support apparatus according to claim 2, wherein the lesion determination unit is further configured to determine occurrence of a detection error when a distance between the pixel of interest and a pixel used to calculate the nearest neighbor vector is greater than a detection error threshold value.

8. The diagnostic support apparatus according to claim 1, wherein the feature quantity calculation unit is configured to calculate a plurality of shift-invariant feature quantities from a pixel of interest in the test image and calculate a test image feature quantity vector having the calculated shift-invariant feature quantities as vector elements,
the base representation unit is configured to calculate the first coefficients and calculate a test coefficient vector having the calculated first coefficients as vector elements, the first coefficients being used to represent the test image feature quantity vector as a linear combination of the base vectors, the base vectors being calculated from a plurality of image feature quantity vectors each having, as vector elements, shift-invariant feature quantities calculated from pixels in each of the normal structural images, and the normal structural images each being a medical image of a normal structure,
the diagnostic support apparatus further comprising
a neighbor vector detection unit configured to detect a predetermined number of normal coefficient vectors starting from a normal coefficient vector that is most similar to the test coefficient vector from among a plurality of normal coefficient vectors each having second coefficients as vector elements, the second coefficients being used to represent each of the image feature quantity vectors as the linear combination of the base vectors, and the lesion determination unit is configured to, for each of the predetermined number of normal coefficient vectors detected by the neighbor vector detection unit, compare a distance between the test coefficient vector and the normal coefficient vector with the determination threshold value, determine that the pixel of interest is in the lesion site when the distance is greater than the determination threshold value, and determine that the pixel of interest is in a normal site when the distance is smaller than or equal to the determination threshold value.

9. A diagnostic support method comprising:

vectorizing a test image into shift-invariant feature quantities, the test image being an image in which presence of a lesion site is unknown;

transforming the shift-invariant feature quantities of the test image into a linear combination of base vectors with first coefficients, the base vectors being represented by eigen vectors calculated through principal component analysis of a plurality of vectors representing shift-invariant feature quantities of a plurality of normal structural images that include no lesion site;

storing in a storage unit second coefficients, the second coefficients being used to transform shift-invariant feature quantities calculated from one of the plurality of normal structural images into a linear combination of the base vectors;

obtained from a result of the transforming and the second coefficients stored in the storage unit is greater than a determination threshold value; and outputting a result of determination of the lesion site.

10. A non-transitory computer-readable recording medium for use in a computer, the recording medium having a computer program recorded thereon for causing the computer to execute the diagnostic support method according to claim 9.

* * * * *